US012409216B2

(12) United States Patent
Choi et al.

(10) Patent No.: US 12,409,216 B2
(45) Date of Patent: Sep. 9, 2025

(54) SEVERE FEVER WITH THROMBOCYTOPENIA SYNDROME VIRUS

(71) Applicant: I.D.BIO., Cheongju-si (KR)

(72) Inventors: Yeo-Jeong Choi, Cheongju-si (KR); Su-Jin Park, Cheongju-si (KR); Young-Il Kim, Daejeon (KR); Min-Ah Yu, Sejong (KR)

(73) Assignee: I.D.BIO., Cheongju-si (KR)

( * ) Notice: Subject to any disclaimer, the term of this patent is extended or adjusted under 35 U.S.C. 154(b) by 0 days.

(21) Appl. No.: 18/348,323

(22) Filed: Jul. 6, 2023

(65) Prior Publication Data

US 2023/0346909 A1 Nov. 2, 2023

Related U.S. Application Data

(63) Continuation of application No. 17/050,602, filed as application No. PCT/KR2019/004857 on Apr. 23, 2019, now Pat. No. 11,738,078.

(30) Foreign Application Priority Data

Apr. 25, 2018 (KR) ........................ 10-2018-0047865

(51) Int. Cl.

| | |
|---|---|
| ***A61K 39/12*** | (2006.01) |
| ***A61P 31/12*** | (2006.01) |
| ***G01N 33/569*** | (2006.01) |
| *A61K 39/00* | (2006.01) |

(52) U.S. Cl.

CPC .............. *A61K 39/12* (2013.01); *A61P 31/12* (2018.01); *G01N 33/569* (2013.01); *A61K 2039/5252* (2013.01); *A61K 2039/6056* (2013.01)

(58) Field of Classification Search

None

See application file for complete search history.

(56) References Cited

FOREIGN PATENT DOCUMENTS

| | | |
|---|---|---|
| KR | 10-2015-0042419 A | 4/2015 |
| KR | 10-2016-0054161 A | 5/2016 |

OTHER PUBLICATIONS

Liu et al., Immunization with Recombinant SFTSV/NSs Protein Does Not Promote Virus Clearance in SFTSV-Infected C57BL/6J Mice, Viral Immunology, 2015, vol. 28, No. 2.*

International Search Report for PCT/KR2019/004857 Aug. 19, 2019 (PCT/ISA/210).

Seok-Min Yun et al., "Molecular genomic characterization of tick and human-derived severe fever with thrombocytopenia syndrome virus isolates from South Korea", PLOS Neglected Tropical Diseases, Sep. 22, 2017, pp. 1-15.

Tomoki Yoshikawa et al., "Phylogenetic and Geographic Relationships of Severe Fever With Thrombocytopenia Syndrome Virus in China, South Korea, and Japan", Phylogenetic Analysis of SFTSV, Sep. 15, 2015, pp. 889-898, vol. 212.

Yonggeng Fu et al., "Phylogeographic analysis of severe fever with thrombocytopenia syndrome virus from Zhoushan Islands, China: implication for transmission across the ocean", Scientific Reports, pp. 1-8, vol. 6, No. 19563.

GenBank Accession ASW22984, RNA-dependent RNA polymerase [Severe fever with thrombocytopenia syndrome virus], Sep. 5, 2017.

GenBank Accession ASW22987, membrane glycoprotein polyprotein [Severe fever with thrombocytopenia syndrome virus], Sep. 5, 2017.

GenBank Accession KY789438, Severe fever with thrombocytopenia syndrome virus isolate CBS segment M, complete sequence, Sep. 5, 2017.

GenBank Accession KY789435, Severe fever with thrombocytopenia syndrome virus isolate CBS segment L, complete sequence, Sep. 5, 2017.

GenBank Accession KY789441, Severe fever with thrombocytopenia syndrome virus isolate CBS segment S, complete sequence, Sep. 5, 2017.

Brennan et al., Reverse Genetics System for Severe Fever with Thrombocytopenia, Syndrome Virus, 2015, vol. 89, No. 6, pp. 3026-3037.

Gen Bank Accession: ASW22984, RNA-dependent RNA polymerase [Severe fever with thrombocytopenia syndrome virus], 2017.

* cited by examiner

*Primary Examiner* — Benjamin P Blumel
(74) *Attorney, Agent, or Firm* — Sughrue Mion, PLLC

(57) ABSTRACT

The present invention relates to a novel genotype of severe fever with thrombocytopenia syndrome viruses and use thereof as an immunogenic composition. The severe fever with thrombocytopenia syndrome viruses of the present invention are genetically different from conventional severe fever with thrombocytopenia syndrome viruses and are novel viruses taxonomically belonging to three sub-groups of genotype B. In view of the vaccine property that specific genotype viruses alone show only limited protective potential, the novel viruses of the present invention may be advantageously used as a vaccine having excellent cross-immunogenicity for SFTSV.

5 Claims, 6 Drawing Sheets

Specification includes a Sequence Listing.

Genotype B(B-1, B-2, B-3) type.

A) L gene

Amino acids site

B) M gene

Amino acids site

SEQUENCE LISTING

```
Sequence total quantity: 24
SEQ ID NO: 1            moltype = DNA  length = 6255
FEATURE                 Location/Qualifiers
misc_feature            1..6255
                        note = severe fever thrombocytopenia syndrome virus B-1 L
                         gene
source                  1..6255
                        mol_type = other DNA
```

-continued

```
                         organism = unidentified
SEQUENCE: 1
atggacttgg aagtgctttg tggtaggata aacgtggaga atgggctgtc tcttggagaa  60
ccaggcctgt acgaccaaat ctacgacagg ccagggctgc cagacctaga tgtgactgtc  120
gatgccacag gtgtgacagt ggacataggg gctgtgccag actcagcatc acaactgggc  180
tcatcaatca atgctgggtt gatcacaatc cagctctctg aagcatataa gatcaatcat  240
gacttcacat tttctggcct gtcaaagaca acagaccgac gcctctcaga ggtattcccc  300
attacccatg atggttctga tgggatgacc cctgatgtga tccacaccag attggatgga  360
actattgtgg tggttgaatt ttcaaccact aggagccata acattggggg cctggaggca  420
gcatatagga caaagataga aaaatatagg gacccaatct caaggcgtgt tgatatcatg  480
gagaacccga gagtcttctt tggtgttatt gtagtctcgt caggaggggt tctgtccaac  540
atgcccctga ctcaggatga ggcagaggag ctcatgtaca ggttctgcat agccaatgaa  600
atctacacta aggctagatc tatggatgca gacattgagc tacagaagag tgaagaagag  660
cttgaggcta tcagcagggc actttcattc ttcagtttgt tcgagcctaa cattgaaaga  720
gtggaaggaa cattccccaa ttcagaaatt gagatgctgg aacagtttct ctcaacacca  780
gctgatgttg acttcatcac caagaccctc aaagcaaaag aggtggaggc ctatgctgat  840
ctttgtgaca gccactacct aaagcctgaa aaaaccattc aggagcgtct agagatcaat  900
agatgtgagg ctattgacaa aactcaggac ctcctagctg gcctacatgc aaggagcaac  960
aagcaaacat cattgaatcg aggacagtc  aaactcccgc cctggctgcc aaagccatca  1020
agtgagtcaa tagacatcaa gaccgactca ggctttggtt ccttaatgga tcatggcgca  1080
tatggtgagc tatgggcaaa gtgccttcta gatgtctcgt taggcaatgt ggagggggta  1140
gtcagtgacc ctgcaaaaga gcttgacatt gctatctctg atgacccaga aaaagacacc  1200
cccaaagagg caaagataac ctataggcga ttcaagcctg ccttaagttc aagtgcccgg  1260
caagaatttt ctctccaagg agtggagggg aagaagtgga agagaatggc agcaaaccag  1320
aagaaagaga aggagtccca tgagacattg agccctttct tggatgttga agacattggg  1380
gatttcctga cattcaacaa tcttcttgca gattcgaggt atggagatga gtccatccag  1440
agagctgtgt caatcttgtt ggaaaaggca tctgccatgc aggacacaga gctcactcat  1500
gctctcaacg actcattcaa gaggaaccta agcagcaatg tggttcagtg gtccctttgg  1560
gtttcctgtt tggcgcagga gctagctagt gctctgaagc agcactgcag ggctggtgag  1620
ttcatcatca agaagctgaa gttctggcct atctatgtca ttatcaagcc gaccaaatcg  1680
tcatctcaca tcttctacag cttagggatc cgcaaggctg acgtgacaag gaggctcact  1740
ggtagagtct tctctgacac cattgatgca ggggaatggg agctaacaga gttcaaaagc  1800
ctgaagacat gtaagctcac gaaccttgtc aacttaccat gcaccatgct gaactcaata  1860
gctttctgga gagagaagct gggcgtggct ccatggctgg tccggaagcc ttgttcagag  1920
ctcagggagc aggtgggcct gaccttcctg atcagtctgg aggacaagtc taagactgag  1980
gagatcatca ccttgacaag gtacacccag atggagggct ttgtctctcc tcccatgctg  2040
cccaaacccc aaaagatgct agggaaactg gatggacctt tgagaaccaa gctacaggtt  2100
tacctcctca ggaagcatct ggattgcatg gtgcgaattg cttctcagcc attcagccta  2160
atcccaagag aggggagagt agaatgggga ggaacattcc atgccatctc aggccggtcc  2220
acaaatcttg agaatatggt gaacagctgg tacattgggt actacaagaa caaagaggag  2280
tcaacagaac taaatgctct cggagaaatg tataagaaga ttgtggagat ggaagaggac  2340
aagcccagca gccctgagtt tctggggtgg ggggacactg attcccctaa gaagcatgaa  2400
ttctcacgga gcttcctgag agctgcttgc tcatctctgg aaagagaaat tgctcagcga  2460
catggaagac aatggaagca gaaccttgag gagcgagtcc tgagagagat tgggaccaag  2520
aacatcctgg accttgcatc catgaaggct actagcaact tttccaaaga ctgggagctc  2580
tactcagaag tccagaccaa agagtaccat aggtccaaac tgctggagaa gatggccaca  2640
ttgattgaga agggggttat gtggtacatt gatgctgtgg gtcaggcatg gaaggcagtt  2700
ctggatgacg ggtgcatgcg aatctgtctc ttcaaaaaga atcagcatgg tggcctcaga  2760
gagatctacg ttatggatgc aaatgcccgg ctcgtgcagt ttggggttga gaccatggct  2820
aggtgtgtct gtgagctgag cccacatgag actgttgcca accctaggct caagaattcc  2880
atcatagaga accatgggct gaagtcagcc cgtagtcttg gccctggctc tataaacata  2940
aactcatcca atgatgccag gaagtggaat caggggcact acacaacaaa gctagctcta  3000
gttctttgtt ggttcatgcc agccaaattc cacagattca tttgggctgc catttccatg  3060
tttcggagaa aaaagatgat ggtggaccta aggtttttag ctcacctcag ttctaaatct  3120
gagtctaggt catctgatcc atttagggaa gcaatgacag acgccttcca tggcaatagg  3180
gaagtctcat ggatggacaa agggcgaact tacataaaga cagagacagg tatgatgcag  3240
ggtatactgc actttacatc cagcctcctc cactcttgtg ttcagagctt ttacaagtct  3300
tatttcgtct cgaaactcaa ggagggctac atgggagaaa gcatcaatgg ggtggtggat  3360
gtcatagaag gctctgacga ctcagcgatc atgatcagca tacgccccaa gtcagacatg  3420
gatgaagtcc gatcaaggtt ctttgttgct aacttactcc actctgtaaa gttcttgaac  3480
cctttgtttg ggatctactc atcagagaaa tcaacagtga acacagtgta ttgtgtcgag  3540
tataactctg aattccattt ccacaggcac ttggttcgac ccacactgag atggatagca  3600
gcatctcacc aaatctcaga gactgaggcc cttgcaagca ggcaagagga ttattcaaac  3660
cttctaaccc agtgcttgga gggaggggcc tcattctctc ttacctacct catacagtgc  3720
gctcagctcc tgcaccacta catgcttcta ggactatgct tacacccctt gtttggaact  3780
ttcatgggga tgctgatatc agacccagat ccagccctag ggttcttcct catggacaac  3840
cctgcattcg caggaggagc aggatttaga ttcaatctgt ggagagcctg caagactaca  3900
gaccttgggc ggaagtatgc atattatttt aatgagatac agggtaaaac aaagggagat  3960
gaggactaca gagctctgga cgccacatca ggaggaaccc tcagccactc tgttatggtg  4020
tactgggggg acaggaagaa gtatcaggcc ttattgaaca ggatgggcct tcctgaggac  4080
tgggtggagc agatagatga gaatcccggt gtcctttaca ggagagctgc caacaagaag  4140
gaactactct taaaactggc agagaaggtt cattcacctg gtgtgactag cagcctgagt  4200
aaagggcatg tagtgcctcg ggtggtggca gcaggagtat accttctctc acgccattgc  4260
tttcgcttta gctcaagcat ccatggaagg ggctcagcac agaaggctag ccttataaaa  4320
ctgttgatga tgtcttctgt ttctgccatg aagcatgggg gctcactaaa ccctaatcag  4380
gagcgaatgc tcttccctca ggctcaagag tatgacagag tatgcacatt gcttgaggag  4440
gttgaacacc taacagggaa atttgttgtt agggagagga acattgtcag gagccgcata  4500
gacttgttcc aagagccagt ggacttgcgg tgcaaggcag aagatctggt gtcagaggtg  4560
tggtttggcc tgaaaaggac taaacttgga ccccgtctcc tcaaggaaga gtgggacaaa  4620
```

-continued

```
cttagggcct catttgcatg gctgagcaca gacccatctg aaacattgag ggatggtcct  4680
tttcttagcc atgtgcagtt taggaacttc atagcccacg ttgatgccaa atcaagatca  4740
gtcaggctcc taggtgcccc cgtaaagaag tcaggtgggg tcaccactat aagccaagta  4800
gtcagaatga acttcttccc aggttttagc ctagaagctg agaagagctt agacaatcag  4860
gaaagacttg agagcatctc catcctcaag catgtcttgt tcatggtctt gaatggccca  4920
tacactgagg agtacaagct ggaaatgatc atagaggcct tctctactct tgtgatacct  4980
cagccatcag aggtcatcag gaaatcaagg accatgactt tgtgcctctt atcaaattac  5040
ttgtctagta ggggtgggtc cattctagac cagattgaga gggcacagtc aggcactcta  5100
gggggcttca gcaagcccca gaagactttc attaggccag gaggtggtat cggctacaag  5160
ggaaagggtg tgtggactgg agtgatggag gacacccatg ttcaaattct gatagatgga  5220
gatgggacta gtaactggct tgaggagatc aggctcagta gtgatgccag actttatgat  5280
gtcattgagt ccatccgaag gttatgtgat gacctcggga tcaacaacag ggtggcatct  5340
gcatatagag gccattgcat ggttaggctg agtggattca agatcaagcc agcatcaagg  5400
actgatggct gcccagtcag gattatggaa aggggcttca ggatcaggga actccaaaac  5460
ccagatgagg tcaagatgag agtgagaggt gacatcctca acctctctgt caccattcaa  5520
gaaggaaggg tcatgaacat tctaagctac aggccgagag acactgatat atcagaatca  5580
gccgcagcat atctctggag caatcgagac ctcttctcct ttgggaagaa ggagccatcc  5640
tgcagctgga tctgcttgaa aactcttgac aattgggcct ggtcacatgc ctcagttctc  5700
ctggcaaatg ataggaagac ccaaggcatt gataataagg ctatggggaa catttttcagg  5760
gactgtctcg agggttctct tagaaagcaa gggctgatga ggtcaaagct cacagagatg  5820
gtggagaaga atgtagttcc tttaacaact caagagcttg tcgacatcct ggaggaggac  5880
atagactttt cagatgtcat agctgtggaa ctctcagagg gatcacttga tattgaatcc  5940
atctttgatg ggcacctat cttgtggtct gctgaggtgg aagagtttgg ggaaggagtg  6000
gtggctgtga gctattccag taagtactat catctaaccc tgatggacca agctgccatc  6060
acaatgtgtg cgatcatggg taaggaaggc tgtagagggc tccttactga gaagagatgc  6120
atggcagcca tacgagagca ggtacggcca ttcctcatat tcctgcaaat ccctgaggat  6180
agcatttctt gggtgtctga tcagttctgc gactccaggg gtcttgatga ggagagcacc  6240
attatgtggg gttga                                                  6255
```

```
SEQ ID NO: 2            moltype = DNA  length = 3222
FEATURE                 Location/Qualifiers
misc_feature            1..3222
                        note = severe fever thrombocytopenia syndrome virus B-1 M
                         gene
source                  1..3222
                        mol_type = other DNA
                        organism = unidentified
SEQUENCE: 2
atgatgaaag tcatctggtt ctcctctctg atctgcttag tcattcaatg cagtggggat  60
acgggtccaa tcatatgcgc agggcccatc cactcaaaca agagtgccaa cataccccac  120
ctgcttggct actctgagaa gatttgtcag atagatcggc tgatacatgt ttcgtcatgg  180
ctgagaaacc attcacaatt tcagggctat gtggggcagc gaggtggacg ctctcaggta  240
agctattacc cagctgaaaa ctcttactca aggtggagtg gacttctaag cccctgtgat  300
gcagattggc ttgggatgct tgttgtgaag aaggccaaag ggtctgatat gatagttcct  360
gggccttcat acaagggaaa agtctttttt gaacggccaa cttttgatgg atacgtaggc  420
tggggctgtg gcagtgggaa gtcaaggaca gagtcagggg agctctgcag ctcagactca  480
gggaccagtt ccggtcttct gccctcagat agggttctct ggataggtga tgttgcttgc  540
cagcctatga cacccatccc tgaggagaca tttctggagc tgaagagttt tagccagagt  600
gaattcccag acatatgcaa aattgatggc attgtgttca accagtgtga gagtgagagt  660
ctacctcaac ccttagatgt tgcgtggatg gatgtaggcc actctcataa aatcatcatg  720
agggagcaca agactaaatg ggtacaagag agctcatcta aggattttgt gtgctacaag  780
gaagggactg ggccatgttc tgaatcagaa gaaaagactt gcaagaccag tggatcatgt  840
agggggggaca tgcagttttg caaggtggca ggttgtgaac atggggaaga agcatctgat  900
gccaagtgta gatgctcact agtgcacaag cccggggaag ttgttgtgtc atatggaggg  960
atgcgtgtca gaccaaagtg ttatggcttc tccagaatga tggcaacact agaggtgaac  1020
ccaccagagc aaaggattgg ccaatgcact ggctgccatc ttgaatgcat aaatgggggt  1080
gtgaggctaa tcactctgac tagtgagctc aagtcagcta ctgtctgtgc ttcccacttt  1140
tgtagttctg ccacaagtgg caagaaaagc acggagattc aatttcactc agggtcatta  1200
gttgggaaaa caacaataca cgtcaaaggg gctttggtgg atggaactga attcacattt  1260
gagggcagtt gcatgttccc agatggttgt gacgcagtgg actgcacatt ctgtcgtgag  1320
tttctaaaaa atcctcagtg ctaccctgca aagaaatggc tgttcatcat tattgtcatc  1380
ctccttggat atgcaggcct catgctactt accaatgtcc ttaaggcaat cggggtttgg  1440
ggatcatggg tcatagctcc agtgaagcta atgtttgcca tcataaagaa actgatgaga  1500
tctgtgagct gcttgatggg gaaattaatg gataggggaa ggcaagtgat ccatgaagaa  1560
ataggggaga atagagaggg caaccaagat gatgttagga tcgagatggc aagacccaga  1620
agggtaaggc attggatgta ctcacctgtc atcctgacta ttctagcaat tgggcttgcc  1680
gagggctgcg atgagatggt ccatgctgac tccaaacttg tttcgtgcaa gcaagggagc  1740
ggaaacatga aggaatgtgt cacaactggg agggcactcc ttcctgcggt gaacccagga  1800
caagaggcat gtctgcactt cacggcacct gggagtccgg actcaaaatg tctcaaaatt  1860
aaggtcaaga ggattaacct aaaatgtaag aagtcatcat catattttgt tcctgatgct  1920
cggtctaggt gtacatctgt gaggagatgt cgctgggcag gagactgcca gtctgggtgc  1980
ccctctcatt tcacgtccaa ctccttctct gatgattggg caggtaaaat ggacagggca  2040
ggtctaggat tcagtgggtg ctctgatgga tgtggaggag cagcctgcgg ctgctttaat  2100
gcagcccctt catgcatctt ttggaggaaa tgggtagaga acccgcatgg gatcatctgg  2160
aaagtatctc catgtgctgc atgggtccca tcagcagtca tagagctaac aatgccctca  2220
ggggaagtga ggacattcca ccccatgagc ggcatcccta cacaagtctt caagggtgtg  2280
agtgtgacgt acttaggctc agatatggag gtgtctggct tgactgacct gtgtgagata  2340
gaagagctca agtccaagaa gctggcatta gcccccctgca atcaggctgg catgggggtt  2400
gtaggcaagg ttggagagat acagtgcagt agcgaggaaa gtgcccgtac cataaaaaaa  2460
```

-continued

```
gatgggtgta tatggaatgc tgaccttgtg ggcatagagc tacgagtgga tgacgctgtg  2520
tgctactcta agatcactag tgtggaggca gttgcaaact actctgccat acccaccact  2580
attggggggc tgaggtttga gagaagccat gacagccagg gtaaaatatc tggtagcccc  2640
ttagatataa cagccataag agggtctttt tcagttaatt atagaggcct tcgactgagc  2700
ctctcagagg ttactgctac ttgcacagga gaggtgacga atgtgagtgg gtgttactct  2760
tgcatgacag gcgccaaagt ctccatcaaa ctgcatagca gcaaaaatag cactgcccat  2820
gtaagatgca aaggggatga gacagcattc agtgtcctag tgggagttca tagctatact  2880
gtcagtctca gctttgacca tgcagtggtc gatgagcagt gccagctgaa ctgtggaggg  2940
catgagagtc aagtgactct aaaaggcaac ctcatcttcc tggatgtccc aaaatttgtg  3000
gatggcagct atatgcagac atatcatagt tctgtgccca caggggccaa catcccaagc  3060
cctacagact ggctgaatgc cttgttcggc aatgggctga gtaggtggat tctgggggta  3120
atagggggttc tactgggggg attggctctc tttttcttaa tcatgtctct gttcaaattg  3180
ggaacaaaac aggtatttcg atcaaggacg aagctggctt aa                      3222

SEQ ID NO: 3           moltype = DNA  length = 738
FEATURE                Location/Qualifiers
misc_feature           1..738
                       note = severe fever thrombocytopenia syndrome virus B-1 NP
                        gene
source                 1..738
                       mol_type = other DNA
                       organism = unidentified
SEQUENCE: 3
atgtcagagt ggtccaggat tgcagtggag tttggtgagc agcagctcaa tttgacggag  60
cttgaggact tcgcgagaga gctggcctat gaaggccttg atcctgcttt gatcatcaag  120
aagctgaagg agacaggtgg ggatgattgg gtgagggata caaagttcat cattgtcttt  180
gccctgactc gaggcaataa gattgtcaag gcatcaggga aaatgtcaaa ctcagggtct  240
aagaggttga tggcactcca agagaagtat ggactggttg agagggcaga aaccaggctc  300
tcaatcactc ctgtgagggt ggcacagagc ctacccactt ggacatgtgc tgctgcagca  360
gccttaaagg agtatcttcc agttgggcca gctgtcatga acctgaaggt cgagaattat  420
cctccagaga tgatgtgcat ggcctttggg tccctgattc caactgcggg ggtgtcagaa  480
gctacaacga agaccctgat ggaggcctac tctctgtggc aagatgcctt cacaaagact  540
atcaatgtga agatgcgcgg agccagtaag acagaggttt acaactcctt cagggatcct  600
ctccatgctg ctgtgaactt cgtctttttc ccccaagatg ttcgggtgaa gtggctgaag  660
gccaagggaa tccttggccc agatggggtc cccagcagag ctgctgaggt tgctgctgct  720
gcttacagaa acctgtaa                                              738

SEQ ID NO: 4           moltype = DNA  length = 882
FEATURE                Location/Qualifiers
misc_feature           1..882
                       note = severe fever thrombocytopenia syndrome virus B-1 NS
                        gene
source                 1..882
                       mol_type = other DNA
                       organism = unidentified
SEQUENCE: 4
atgtcgctga gcaaatgctc caacgttgac ctcaaatctg tggcaatgaa tgccaacact  60
gtcaggcttg agccatctct aggagagtac cccactctta ggagagacct cgttgaatgc  120
tcttgtagtg tgttgactct atcaatggtt aagaggatgg gcaagatgac caacacagta  180
tggttgtttg gtaacccaaa aaatcctctt caccagcttg agcctggact cgagcagctg  240
ttggacatgt actacaagga catgaggtgc tactcccaga gagagctgag tgctcttagg  300
tggcctagtg ggaagccatc tgtatggttc ctgcaggcag ctcatatgtt cttctccatc  360
aagaacagct gggcaatgga aaccggcaga gagaattggc ggggcctctt ccacaggata  420
acaaaaggca aaaagtatct ttttgaagga gacatgatat tggattctct tgaggccata  480
gagaagcgaa ggcttagact tgggctacct gagatcctaa taactggact atccccgatt  540
ctggatgtgg ccctcctcca gatagagtca cttgcaaggc taagaggcat gagcttgaac  600
caccacttat tcacatcttc ctcattgcgt aagcctttgt tggactgttg ggacttcttt  660
attcctatcc ggaaaaagag gacagatggc tcatacagta tcttggatga ggatgatgaa  720
cttggggtcc ttcaaggtta cccatatctg atggcacact atttgaatag gtgcccattc  780
cacaacctca tcaggtttga tgaagagctg agaactgcag ccctaaacac catctgggga  840
agagattggc cggccattgg tgacctcccg aaggaggtct aa                      882

SEQ ID NO: 5           moltype = DNA  length = 6255
FEATURE                Location/Qualifiers
misc_feature           1..6255
                       note = severe fever thrombocytopenia syndrome virus B-2 L
                        gene
source                 1..6255
                       mol_type = other DNA
                       organism = unidentified
SEQUENCE: 5
atgaacttgg aagtgctttg tggtaggata aacgtggaga atgggctgtc tcttggagaa  60
ccaggcctgt acgaccaaat ctacgacagg ccagggctgc cagacctaga tgtgactgtc  120
gatgccacag gtgtgacagt ggacataggg gctgtaccag actcagcatc acaactgggc  180
tcatcaatca atgctgggtt gatcacaatc cagctctctg aagcatataa gatcaatcat  240
gacttcacat tttctggcct gtcaaagaca acagaccgac gcctctcaga ggtattcccc  300
attacccatg atggttcaga tgggatgacc cctgatgtga ttcataccag attggatgga  360
accattgtgg tggttgaatt ttcaaccact aggagccata acattggggg cctggagacg  420
gcatatagaa caaagataga gaaatatagg gacccaatct caaggcgtgt tgatatcatg  480
```

-continued gagaacccga gggtcttctt tggcgttatt gtagtctcgt caggaggggt tctatccaac 540
atgcccctga ctcaggatga ggcagaggag ctcatgtaca ggttctgcat agccaatgag 600
atctacacca aggctagatc tatggatgca gacattgagc tacagaagag tgaagaagag 660
cttgaggcta ttagcagggc actgtcattc ttcagtttgt ttgagcctaa cattgaaaaa 720
gtggaaggaa cattccccaa ttcagaaatc gagatgctgg aacagtttct ttcaacacca 780
gctgatgttg acttcatcac taagacactc aaagcaaaag aggtggaggc ctatgctgat 840
ctttgtgaca gccactacct aaagcctgaa aaaaccattc aggagcggct agagatcaat 900
agatgtgagg ctattgataa aactcaggac ctcctagcta gcctgcatgc aaggagcaac 960
aaacaaacat cactgaatcg agggacagtc aaactcccgc cctggctacc aaagccatca 1020
agtgagtcaa tagacatcaa gaccgactca ggctttggtt ccttaatgga ccatggcgca 1080
tatggtgagc tgtgggcaaa gtgccttcta gatgtctcgc tgggcaatgt ggagggggta 1140
atcagtgacc ctgcaaaaga acttgacatt gctatctctg atgatccaga aaaagatacc 1200
cccaaagaag caaagataac ctataggcga ttcaagcctg ccttaagttc aagtgcccgt 1260
caggaatttt ctctccaagg agtggaggga aagaagtgga agagaatggc agcaaaccag 1320
aagaaagaga aggagtccca tgaggcattg agccccttct tggatgttga ggacattggg 1380
gatttcctaa cattcaacaa tcttcttgca gattcaaggt atggagatga gtccgtccag 1440
agagctgtgt caatcctgtt ggagaaggca tctgccatgc aaaacacaga gctaactcat 1500
gccctcaatg actcattcaa gaggaaccta agcagtaatg tggttcagtg gtccctctgg 1560
gtctcctgtt tagcacagga gctagctagt gctctgaagc agcactgcag ggctggtgag 1620
ttcatcatca agaagttgaa gttctggcct atctatgtca tcatcaagcc gaccaaatcg 1680
tcttcccata tcttctacag cttagggatc cgcaaggctg atgtgacaag gaggctcact 1740
ggcagagtct tctctgacac cattgatgct ggggaatggg agctaacaga gttcaaaagc 1800
ctgaagacat gcaagctcac gaaccttgtc aacttaccat gcaccatgct gaactcaata 1860
gctttctgga gagagaagct gggcgtggct ccatggctgg ttcggaagcc ttgttcagag 1920
ctcagagagc aggtgggcct gaccttcctg atcagtctgg aggacaagtc taagactgag 1980
gagatcatca ccttgacaag gtacacccag atggagggct ttgtctctcc tcccatgctg 2040
cctaagcccc aaaagatgct agggaaactg gatggacctt tgagaactaa gttacaggta 2100
tacctcctca ggaagcatct ggattgcatg gtgcgaattg cttctcagcc attcagccta 2160
atccctagag aggggagggt agaatgggga ggaacattcc atgccatctc aggccggtcc 2220
acaaaccttg agaatatggt gaacagctgg tacattgggt actacaagaa caaagaggag 2280
tcaacagagc taaatgctct cggagaaatg tataagaaga ttgtagagat ggaagaggac 2340
aagcccagta gccctgagtt tctagggtgg ggggacactg attcccctaa gaagcatgaa 2400
ttctcacgga gcttcctcag agctgcttgc tcatctctgg agagagaaat tgctcagcga 2460
catggaagac aatggaagca gaaccttgag gagcgtgtcc tgagagagat tgggaccaag 2520
aacatcctgg accttgcatc catgaaggct acaagcaact tttccaaaga ctgggagctc 2580
tactcagagg tccagaccaa agagtaccat aggtccaaac tgctggagaa gatggccaca 2640
ttgatagaga agggggttat gtggtacatt gatgctgtgg gccaggcatg gaaggcagtt 2700
ctagatgacg ggtgcatgcg aatctgtctc ttcaaaaaga atcagcatgg tggtctcaga 2760
gagatctacg ttatggatgc aaatgcccgg ctcgtgcagt ttggggttga gaccatggct 2820
aggtgtgtct gtgagttgag cccacatgag actgttgcca accctagact caagaattcc 2880
atcatagaga accatgggct gaagtcagcc cgtagtcttg gtcctggctc tataaacata 2940
aactcatcca atgacgccaa gaagtggaat caggggcact acacaacaaa gctagctcta 3000
gttctttgtt ggttcatgcc agccaaattc cacagattca tttgggccgc catttccatg 3060
tttcggagaa aaaagatgat ggtggaccta aggtttttag ctcacctcag ttctaaatct 3120
gagtctaggt catctgaccc gtttagggaa gcaatgacag acgctttcca tggtaatagg 3180
gaagtctcat ggatggacaa agggcgaact tacataaaga cagagacagg aatgatgcag 3240
ggcatactgc actttacatc cagcctcctt cactcttgtg ttcagagctt ttacaagtct 3300
tatttcgtct cgaagcttaa ggagggctac atgggggaaa gcatcaatgg ggtggtggat 3360
gtcatagaag gctctgacga ctctgcgatc atgatcagca tacgccctaa gtcagacatg 3420
gatgaagtcc gatcaaggtt ctttgttgct aacttgctcc actctgtcaa gttcttgaac 3480
cctttgtttg gtatttactc atcagagaaa tcaacagtga acacagtgta ttgtgttgag 3540
tataactctg aattccactt ccacaggcac ttggtcagac ccacactgag atggatagca 3600
gcgtctcacc aaatctcaga gactgaagcc cttgcaagca ggcaagagga ttactccaac 3660
cttctaaccc agtgcttgga aggaggggcc tcattctctc ttacctacct tatacagtgc 3720
gctcagctcc tgcaccacta catgctccta ggactatgct tacatccctt gtttggaact 3780
ttcatgggga tgctgatatc agacccagat ccagccctag ggttcttcct catggacaac 3840
cctgcattcg caggggggagc aggatttagg ttcaatctgt ggagggcctg caagactaca 3900
gaccttgggc ggaagtatgc atattatttt aatgagatac agggtaaaac aaagggagat 3960
gaggattaca gagctctgga cgccacatcg ggaggaactc tcagccactc tgtcatggtg 4020
tactgggggg acaggaagaa gtatcaggcc ttattgaaca ggatgggcct tcctgaagac 4080
tgggtggagc agatagatga gaatcctgga gtcctttaca ggagagctgc caacaaaaag 4140
gaactactct taaaactggc agagaaggtt cattcaccag gtgtgactag cagcctgagt 4200
aaagggcatg tagtgcctcg ggtggtggca gcaggagtat accttctctc acgccactgc 4260
tttcgcttta gctcaagtat ccatggaagg ggctcagcac agaaggctag tcttataaaa 4320
ctgctgatga tgtcttctat ttctgccatg aagcacgggg gctcactaaa ccctaatcag 4380
gagcgaatgc tcttccctca ggcccaggag tatgacagag tatgcacatt gcttgaggaa 4440
gttgagcacc taacagggaa atttgttgtt agggagagaa acattgtcag gagccgtata 4500
gacttgttcc aagagccagt ggacttgcgg tgcaaggcag aagatctggt gtcagaggtg 4560
tggtttggcc tgaaaaggac taagcttgga ccccgtctcc tcaaggaaga gtgggacaaa 4620
cttagggcct catttgcatg gctgagcaca gacccatctg aaacattgag ggatggccct 4680
tttcttagcc atgtgcagtt tagaaacttc atagcccatg ttgatgccaa atcaagatca 4740
gtcaggctcc taggtgcccc cgtaaagaag tcaggtgggg tcaccactat aagccaagta 4800
gtcaggatga acttcttccc tggttttagc ctagaagctg agaagagctt agacaatcag 4860
gaaagacttg agagcatctc catcctcaag catgtcttgt tcatggtctt gaatggccca 4920
tacactgagg agtacaagct ggaaatgatc atagaggcct tctctactct tgtgataccct 4980
cagccatcag aggtcatcag gaaatcaagg accatgactt tatgcctctt atcgaattac 5040
ttgtctagta ggggtgggtc cattctagac cagattgaga gggcacagtc aggcactcta 5100
gggggcttca gcaagcccca gaagacattc attaggccag gaggtggtat tggctacaag 5160
ggaaaaggtg tgtggactgg agtgatggag gacacccatg ttcaaatctt gatagatgga 5220

```
gatgggacta gtaactggct tgaggagatc aggctcagta gtgatgccag gctttatgat  5280
gtcattgaat ccatccgaag gttatgtgac gaccttggga tcaataacag ggtggcatct  5340
gcatatagag gtcattgcat ggttaggctg agtgggttca agatcaagcc agcatcaagg  5400
actgacggct gtccagtcag gattatggaa aggggcttca ggatcaggga acttcaaaac  5460
ccagatgagg tcaagatgag agtgaggggt gacatcctca acctttcagt caccatacaa  5520
gaaggaaggg tcatgaacat tctaagctac aggcctagag acactgatat atcagagtca  5580
gccgcagcat acctctggag caatcgagac ctcttctcct ttgggaagaa ggagccatcc  5640
tgcagctgga tctgcttgaa aactcttgac aattgggcct ggtcacatgc ctcagttctc  5700
ctggcaaatg ataggaagac ccaaggcatt gataatagag ccatggggaa cattttcagg  5760
gactgtctcg agggctctct tagaaagcag gggctgatga ggtcaaaact cacagagatg  5820
gtggagaaga atgttgttcc tttaacaact caagagcttg tcgacatctt ggaggaggac  5880
atagactttt cagatgtcat agctgtggag ctctcagagg gatcacttga cattgaatcc  5940
atctttgatg gggcacctat cttgtggtct gctgaggtgg aagagttcgg ggaaggagtg  6000
gtggctgtga gctattccag taagtactat catctaaccc tgatggatca ggctgccatc  6060
acaatgtgtg cgatcatggg taaggaaggc tgtagagggc tccttactga gaagagatgc  6120
atggcagcca tacgagagca ggtacggcca ttcctcatat tcctgcaaat tcctgaggac  6180
agcatttctt gggtatctga tcagttctgt gactccaggg gtcttgatga agagagcacc  6240
attatgtggg gttga                                                   6255
```

```
SEQ ID NO: 6            moltype = DNA  length = 3222
FEATURE                 Location/Qualifiers
misc_feature            1..3222
                        note = severe fever thrombocytopenia syndrome virus B-2 M
                         gene
source                  1..3222
                        mol_type = other DNA
                        organism = unidentified
SEQUENCE: 6
atgatgaaag tcatctggtt ctcctctctg atctgcttag tcattcaatg cagtggggac  60
acgggcccaa tcatatgcgc agggcccatc cactcaaaca agagtgccga catacccac  120
ctgcttggtt actctgagaa gatttgtcag atagatcggc tgatacatgt ttcgtcatgg  180
ctgagaaacc attcacaatt tcagggctac gtggggcagc gaggtggacg ctctcaggtg  240
agttacttcc cagctgaaaa ctcttactca aggtggagtg ggcttctaag cccctgtgat  300
gctgattggc ttgggatgct tgtcgtgaag aaggccaagg ggtctgatat gatagttcct  360
gggccttcat acaagggaaa agtctttttt gaacggccaa cttttgatgg atatgttggc  420
tggggctgtg gcagtgggaa gtcaaggact gagtcaggag agctctgcag ctcagactca  480
gggaccagtt ccggtcttct gccctcaaat agggttctct ggataggtga tgttgcttgc  540
cagcctatga cacccatccc tgaagagaca tttctggagc tgaagagttt tagccagagt  600
gaatttccag atatatgcaa aattgatggc attgtgttca accagtgtga gagtgagagc  660
ctacctcagc cctttgatgt tgcttggatg gatgttggcc actctcataa aatcatcatg  720
agggagcaca agaccaaatg ggtacaagag agctcatcta aggattttgt gtgctacaag  780
gaagggactg ggccgtgttc tgaatcagaa gaaaagactt gcaagaccag tggatcatgt  840
agggggggaca tgcagttttg caaggtggca ggttgtgaac atggggaaga gacatctgag  900
gccaaatgca gatgctcact agtgcacaag cccggggaag ttgttgtgtc atatggaggg  960
atgcgtgtca gaccaaaatg ctatggtttc tccagaatga tggcaacact agaggtgaac  1020
ccaccagagc aaaggattgg ccaatgtact ggctgccatc tagaatgcat aaatgggggt  1080
gtgaggataa tcactctaac tagtgagctc aagtcagcta ctgtctgtgc ttcccacttt  1140
tgtagttctg ccacaagtgg caagaaaagc acggagattc aattccactc agggtcatta  1200
gttgggaaaa cagcaattca cgtcaaaggg gcattggtgg atggaactga attcacattt  1260
gaaggcagtt gcatgttccc agatggttgt gacgcagtgg actgcacatt ctgtcgtgag  1320
tttctaaaaa atcctcagtg ctaccctgca aagaaatggt tgttcatcat tattgtcatc  1380
ctccttggat atgcaggcct catgctactc accaatgtcc ttaaggcaat cggggtttgg  1440
gggtcatggg tcatagctcc agtgaagcta atgtttgcca tcataaagaa actgatgaga  1500
tctgtgagct gcttgatggg gaaattgatg gataggggaa ggcaagtgat ccatgaagaa  1560
ataggggaga atagagaggg caaccaagat gatgttagga tcgagatggc aaggcctaga  1620
agggtaaggc actggatgta ctcacctgtc atcctgacta ttctagcaat tgggcttgct  1680
gaggggtgcg atgagatggt ccatgcagat tctaaacttg tttcgtgcaa gcaagggagc  1740
ggaaatatga aggaatgtgt cacaactggg agggcgctcc ttcctgcggt gaacccaggg  1800
caagaggcat gtctgcactt cacagcacca gggagtccgg actcaaaatg tctcaaaatc  1860
aaagttaaga ggatcaacct gaaatgcaag aagtcatcat catatttcgt tcctgatgct  1920
cggtccaggt gtacatctgt gaggagatgc cgctgggcag gagactgtca gtctgggtgc  1980
ccctctcatt tcacgtccaa ctccttttct gacgattggg caggtaaaat ggacagggct  2040
ggtctaggat tcagtgggtg ctctgatgga tgtggaggag cagcctgcgg ctgctttaat  2100
gcggcccctt catgcatctt ctggaggaaa tgggtagaga atccacatgg gatcatctgg  2160
aaagtatctc catgtgctgc atgggtccca tcagcagtca tagagcttac aatgccctcg  2220
ggggaagtga ggacattcca ccccatgagc ggcatcccta ctcaagtctt caagggtgtg  2280
agtgtgactt atttgggctc agatatggag gtatctggct tgactgatct gtgtgaaata  2340
gaagagctca agtccaagaa gctggcatta gctccctgca atcaggctgg catgggggtt  2400
gtaggcaagg ttggagagat acagtgcagt agtgaggaaa gtgcccgtac cataaaaaaa  2460
gatgggtgta tatggaatgc tgacctcgtg ggcatcgagc tacgagtgga tgacgctgtg  2520
tgctactcta agatcactag tgtggaggca gttgcaaact actctgccat acccaccact  2580
attgggggac tgaggtttga gagaagccat gacagccagg gcaaaatatc tggtagcccc  2640
ttggacatca cagccataag agggtctttt tcagttaact atagaggcct tcgactgagc  2700
ctctcagaaa ttactgctac ttgcacaggg gaggtgacaa atgtgagtgg gtgttactct  2760
tgcatgacag gcgccaaagt ctccatcaaa ctgcatagca gcaaaaatag cactgcacat  2820
gtaaggtgca aaggggatga gactgcgttc agtgtcctgg agggagttca tagctatact  2880
gtcagcctca gttttgacca tgcagtggtc gatgagcagt gccagctgaa ctgtgggggg  2940
catgagagcc aagtgactct aaaaggcaac ctcatcttcc tggatgtccc aaaattcgta  3000
gatggcagct acatgcagac atatcatagc tctgtaccca caggagcaaa tatcccaagc  3060
```

-continued

```
ccaacagact ggctgaatgc cctgtttggc aatgggctga gtaggtggat tctgggggtg  3120
ataggggttc tactgggggg attagctctc tttttcctaa tcatgtcttt gttcaaactg  3180
ggaacaaaac aggtatttcg atcaaggacg aagctggctt ag                     3222

SEQ ID NO: 7            moltype = DNA  length = 738
FEATURE                 Location/Qualifiers
misc_feature            1..738
                        note = severe fever thrombocytopenia syndrome virus B-2 NP
                         gene
source                  1..738
                        mol_type = other DNA
                        organism = unidentified
SEQUENCE: 7
atgtcagagt ggtccaggat tgcagtggag tttggtgagc agcagctcaa tttgactgag  60
cttgaagatt ttgcgagaga gctggcctat gaaggccttg atcctgcatt gatcatcaag  120
aagctgaagg agacaggtgg agatgattgg gtgagggaca caaagttcat cattgtcttt  180
gccctgactc gaggcaacaa gatcgtcaag gcatcaggga aaatgtcaaa ctctgggtct  240
aagaggttga tggcactcca agagaaatat gggctggttg agagggcaga aaccaggctc  300
tcaatcactc ctgtgagggt tgcacagagc cttcccactt ggacatgtgc tgcagcagca  360
gccctaaagg agtatctccc agtggggcca gctgtcatga acctgaaggt cgaaaattat  420
ccccctgaga tgatgtgcat ggcctttggg tccctgattc caactgcagg ggtatctgaa  480
gccacaacga agaccctgat ggaggcctac tctctgtggc aagatgcctt caccaagact  540
atcaatgtaa agatgcgcgg agccagcaag acagaggttt acaactcttt cagggatcct  600
ctccatgctg ctgtgaactc tgtcttcttt cccaatgatg tccgggtgaa gtggctgaag  660
gccaagggaa tccttggccc agatggggtc cccagcagag ctgctgaggt tgctgccgct  720
gcttacagaa acctgtaa                                                738

SEQ ID NO: 8            moltype = DNA  length = 882
FEATURE                 Location/Qualifiers
misc_feature            1..882
                        note = severe fever thrombocytopenia syndrome virus B-2 NS
                         gene
source                  1..882
                        mol_type = other DNA
                        organism = unidentified
SEQUENCE: 8
atgtcgctga gcaaatgctc caacgttgac ctcaaatctg ttgcaatgaa tgccaacact  60
gtcaggcttg agccatctct aggagagtac cccactctta ggagagacct cgttgaatgc  120
tcttgtagtg tgttgactct atcaatggtc aagaggatgg gcaagatgac caacacagta  180
tggctatttg gcaacccaaa gaatcctctt caccagcttg agcctggact cgagcagctg  240
ttagacatgt actacaagga catgaggtgc tactcccaga gagagctgag tgctcttagg  300
tggcctagtg ggaagccatc tgtatggttc ctacaggcag ctcacatgtt cttctccatc  360
aagaacagct gggcaatgga aaccggtaga gagaactggc ggggcctctt ccacaggata  420
acaaaaggcc aaaagtatct ttttgaaggg gacatgatat tggattctct tgaggccata  480
gagaagcgaa ggcttagact agggttacct gagatcctaa taactgggct atccccaatt  540
ctggatgtgg ccctcctcca gatagagtca cttgcaaggc taagaggaat gagcttgaac  600
caccacttat tcacttcttc ctcattgcgt aagcctctat tagactgttg ggacttcttt  660
attcccatcc gcaaaaagaa gacagatggc tcatacagtg tcctggatga ggatgatgag  720
cctgggatcc ttcaaggtta tccatatctg atggcacact atttgaatag gtgcccattc  780
cacaacctca tcaggtttga tgaagagctg agaactgcag ccctaaacac catctgggga  840
agagattggc cagccattgg tgacctcccg aaggaggtct aa                     882

SEQ ID NO: 9            moltype = DNA  length = 6255
FEATURE                 Location/Qualifiers
misc_feature            1..6255
                        note = severe fever thrombocytopenia syndrome virus B-3 L
                         gene
source                  1..6255
                        mol_type = other DNA
                        organism = unidentified
SEQUENCE: 9
atgaacttgg aagtgctttg tggtaggata aacgtggaga atgggctgtc tcttggagaa  60
ccaggcctgt acgaccaaat ctacgacagg ccagggctgc cagacctaga tgtgactgtc  120
gatgccatag gtgtgacagt ggacataggg gctgtgccag actcagcatc acaactgggt  180
tcatcaatca atgctgggtt gatcacaatc cagctctctg aagcatataa gatcaatcat  240
gatttcacgt tttctggcct gtcaaagaca acagaccgac gcctctcaga ggtattcccc  300
attacacatg atggttctga tgggatgacc cctgatgtga tccacaccag attggatgga  360
accattgtgg tggttgaatt ttcaactact aggagccata acattggggg tctggaggca  420
gcatacagga caaagataga aaaatatagg gaccctatct caaggcgtgt tgatatcatg  480
gagaacccga gggtcttctt tggcgtcatt gtggtctcgt cagggggagt tctgtccaac  540
atgcccctga ctcaggatga ggcagaggag ctcatgtaca ggttctgcat agccaatgag  600
atctacacta aggctaggtc tatggatgca gacattgagc tgcagaagag cgaagaagag  660
cttgaggcta ttagcagggc actatcattc ttcagtttgt ttgagccaaa cattgaaaga  720
gtggaaggaa cattccctaa ttcggaaatc gagatgctgg aacagtttct ctcaactcca  780
gctgatgttg acttcatcac caagaccctc aaagcaaaag aggtggaggc ctatgctgat  840
ctttgtgaca gccactatct aaagcctgaa aaaaccattc aggagcggct agagatcaat  900
agatgtgagg ctattgacaa gactcaggac ctcctagcta gcctgcatgc aaggagcaac  960
aagcaaacat cattgaatcg agggacagtc aagctcccgc cctggctacc aaagccatca  1020
agtgagtcaa tagacatcaa gactgactca ggctttggtt ccttaatgga tcatggcaca  1080
```

-continued

```
tatggagagc tgtgggcaaa gtgcctccta gatgtctcgc tgggcaatgt ggaggggggta 1140
gtcagtgacc ctgcaaaaga acttgacatt gctatctctg atgatccaga aaaagatacc 1200
cccaaagagg caaagataac ctataggcgg ttcaagcctg ccttgagctc aagtgcccgt 1260
caagaatttt ctctccaagg agtggagggg aagaagtgga agagaatggc agcaaaccag 1320
aagaaagaga aggagtccca tgagacattg agcccttttct tggatgttga agacattggg 1380
gatttcctaa cattcaacaa tcttctcgca gattcgaggt atggagatga gtccgtccag 1440
agagctgtgt caatcttgtt ggaaaaggca tctgccatgc aagacacaga gctcactcat 1500
gccctcaacg actcattcaa gaggaaccta agcagcaatg tggttcagtg gtccctttgg 1560
gtctcctgtc tagcacaaga gctagctagt gctctgaagc agcactgcag ggctggtgag 1620
ttcatcatca agaagctgaa gttctggcct atctatgtca ttatcaagcc gaccaaatcg 1680
tcatcccata tcttctacag cttagggatc cgcaaggctg atgtgacaag gaggctcact 1740
ggcagagtct tctctgacac cattgatgct ggggaatggg agctaacaga gttcaagagc 1800
ctgaagacat gcaagctcac caaccttgtc aacttgccat gcaccatgct gaactcaata 1860
gctttctgga gagagaagct gggcgtggct ccatggctgg ttcggaagcc ttgttcagag 1920
ctcagagagc aggtgggcct gaccttcttg atcagtttgg aggacaagtc taagactgag 1980
gagatcatca ccttgacaag gtacactcaa atggagggct tcgtctctcc tcctatgctg 2040
cctaagcccc aaaagatgct agggaaactg gatgggcctt tgagaactaa gctacaggta 2100
tacctcctca ggaagcatct ggattgcatg gtgcgaattg cttcccagcc attcagcctg 2160
atccctagag aggggagggt agaatgggga gggacattcc atgccatctc aggccggtcc 2220
acaaaccttg agaatatggt gaacagctgg tacattgggt actacaagaa caaagaggag 2280
tcaacagagc taaatgctct tggagaaatg tataagaaga ttgtggagat ggaagaggac 2340
aagcccagca gccctaagtt tctagggtgg ggggacactg attcccctaa gaagcatgaa 2400
ttctcacgga gcttcctcag agctgcttgc tcatctctgg agagagaaat tgctcagcga 2460
catggaagac aatggaagca gaaccttgag gagcgtgtcc tgagagagat tggaaccaag 2520
aacatcctag accttgcatc catgaaggct acaagcaact tttccaaaga ctgggagctc 2580
tactcagaag tccagaccaa agagtaccat aggtccaaat tgctggagaa gatggccaca 2640
ttgattgaga agggggttat gtggtacatt gatgctgtgg gccaggcttg gaaggcagtt 2700
ctagatgacg ggtgcatgcg aatctgtctc ttcaaaaaga atcagcatgg tggcctcaga 2760
gagatctacg ttatggatgc aaatgcccgg ctcgtgcagt ttggggttga gaccatggct 2820
aggtgtgtct gtgagctgag cccacatgag actgttgcca atcctaggct taagaattcc 2880
atcatagaga accatgggct gaagtcagcc cgtagccttg gccctggctc tataaacata 2940
aactcatcca atgatgccaa gaagtggaat caggggcact acacaacaaa gctagctcta 3000
gttctttgtt ggttcatgcc agccaaattc cacagattca tttgggctgc catttccatg 3060
tttcggagaa aaaagatgat ggtggaccta aggtttttag ctcacctcag ttctaaatct 3120
gagtccaggt catctgatcc atttagggaa gcaatgacag acgcattcca tggaaatagg 3180
gaagtctcat ggatggacaa ggggcgaact tacataaaga cagagacagg gatgatgcag 3240
ggcatactgc actttacatc cagcctcctc cactcttgtg ttcagagttt ttacaagtct 3300
tatttcgtct cgaagctcaa ggagggctac atgggggaaa gcatcagtgg ggtggtggat 3360
gtcatagaag gttctgacga ctcagcgatc atgatcagca tacgccctaa gtcagatatg 3420
gatgaagtcc gatcaaggtt ttttgttgct aacctgctcc actctgtcaa attcttgaac 3480
cctttgtttg ggatttactc atcagagaag tcaacagtga acacagtgta ttgtgtcgag 3540
tataactctg aattccattt ccacaggcac ttggttagac ccacactgag atggatagca 3600
gcgtctcacc aaatctcaga gactgaagcc cttgcaagca ggcaagagga ttactccaac 3660
cttctaaccc agtgcttgga aggaggggcc tcattctctc ttacctacct catacagtgc 3720
gctcagctcc tacaccacta catgcttcta ggactatgct tgcatccctt gtttggaacc 3780
ttcatgggga tgctgatatc agacccagat cctgccctag gattcttcct catggacaac 3840
cctgcattcg caggaggagc aggatttaga ttcaatctgt ggagagcctg caagaccaca 3900
gaccttgggc ggaagtatgc atattacttc aatgagatac agggtaaaac aaagggagat 3960
gaggactaca gagctctgga cgccacatcg ggaggaactc tcagccactc tgttatggtg 4020
tactgggggg acaggaagaa gtatcaggcc ttattgaaca ggatgggcct tcctgaagac 4080
tgggtggagc agatagatga gaatcctgga gtcctttaca ggagagctgc caacaagaag 4140
gaactactct taaaactggc agagaaggtt cattcacctg gtgtgactag cagcctgagt 4200
aaagggcatg tagtgcctcg ggtggtggca gcaggagtat accttctctc acgccactgc 4260
tttcgcttta gctcaagcat ccatggaagg ggctcagcac agaaggctag tctcataaaa 4320
ctgctgatga tgtcttctat ttctgccatg aaacacgggg gctcattaaa ccccaatcag 4380
gagcgaatgc tcttccctca ggctcaagag tatgatagag tatgcacatt gcttgaggaa 4440
gttgaacacc taacagggaa atttgttgtt agggagagaa acattgtcag gagccgcata 4500
gacttgttcc aagagccagt tgacttgcgg tgtaaggcag aagatctggt gtcagaggtg 4560
tggtttggcc tgaaaaggac taagcttgga ccccgtctcc tcaaggaaga gtgggacaaa 4620
cttagggcct catttgcatg gctgagcaca gacccatctg aaacattgag ggatggtcct 4680
tttcttagcc atgtgcagtt taggaacttc atagcccacg ttgatgccaa atcaagatca 4740
gtcaggctcc taggtgcccc cgtgaagaag tcaggtgggg taaccaccat aagccaagta 4800
gtcagaatga acttcttccc tggttttagc ctagaagctg agaagagctt agacaatcag 4860
gagagacttg agagcatctc catcctcaag catgtcttgt tcatggtctt gaatggccca 4920
tacactgagg agtacaagct ggacatgatc atagaggcct tctctactct tgtgatacct 4980
cagccatcag aggtcatcag gaaatcaagg accatgactt tatgcctctt atcgaattac 5040
ttgtctagta ggggtgggtc cattctagac cagattgaga gggcacagtc aggcactcta 5100
gggggattca gcaagcccca gaagacattc atcaggccag gaggtggtat tggctacaag 5160
ggaaaaggtg tgtggactgg agtgatggag gacacccatg ttcaaattct gatagatgga 5220
gatgggacta gcaactggct tgaggagatc aggctcagta gtgatgccag gctttatgat 5280
gtcattgaat ccatccggag gttatgtgat gaccttggga tcaacaacag ggtggcatcg 5340
gcatataggg gtcattgcat ggttagactg agtggattca agatcaagcc agcatcaagg 5400
actgacggct gtccagttag gattatggaa aggggcttca ggatcagaga gcttcaaaac 5460
ccagatgagg tcaagatgag agtgaggggt gacattctca acctctctgt taccatacaa 5520
gaaggaagag tcatgaacat tctgagctac aggccgagag acactgatat atcagagtca 5580
gcagcagcat acctatggag caatcgagac ctcttctcct ttgggaagaa ggagccatcc 5640
tgcagctgga tctgcttgaa aactcttgac aattgggcct ggtcacatgc ctcagttctc 5700
ctggcaaatg ataggaagac ccaaggcatt gataatagag ctatggggaa catttcagg 5760
gactgtctcg agggttccct cagaaagcaa gggctgatga ggtcaaagct cactgagatg 5820
```

```
gtggagaaga atgtggttcc tttaacaact caagagcttg tcgatatcct ggaggaggat  5880
atagactttt cagatgtcat agctgtggag ctctcagagg gatcacttga cattgagtcc  5940
atctttgatg gagcacctat cttgtggtct gctgaggtgg aagagtttgg agaaggagtg  6000
gtagctgtga gctattccag taagtactat catctaaccc tgatggacca agctgccatc  6060
acaatgtgtg cgatcatggg taaggaggc tgtagagggc tcctcactga gaagagatgc  6120
atggcagcca tacgagagca ggtaaggcca ttcctcatat tcctgcaaat ccctgaggac  6180
agcatttctt gggtgtctga tcagttctgc gactccaggg gtcttgatga agagagcacc  6240
attatgtggg gttaa                                                  6255

SEQ ID NO: 10          moltype = DNA  length = 3222
FEATURE                Location/Qualifiers
misc_feature           1..3222
                       note = severe fever thrombocytopenia syndrome virus B-3 M
                        gene
source                 1..3222
                       mol_type = other DNA
                       organism = unidentified
SEQUENCE: 10
atgatgaaag tcatctggtt ctcctctctg atctgcttag tcattcaatg cagtggggat  60
acgggcccaa tcatatgcgc tgggcccatc cactcaaaca agagcgccaa catacccac  120
ctgcttggtt actctgagaa aatttgtcag atagatcggc ttatacatgt ttcgtcatgg  180
ctgagaaacc attcacaatt tcagggctac gtggggcagc gaggtggacg ctctcaggtg  240
agttactacc cagctgaaaa ctcttactca aggtggagtg gacttctaag cccctgtgat  300
gctgattggc ttgggatgct tgtcgtgaag aaggccaagg ggtctgatat gatagttcct  360
gggccttcat acaaagggaa agtcttcttt gaacggccaa cttttgatgg atatgtgggc  420
tggggctgtg gtagtgggaa gtcaaggaca gagtcaggtg agctctgcag ctcagactca  480
gggaccagtt ctggtctact gccctcaaat agggttctct ggataggtga tgttgcttgc  540
cagcctatga cacccatccc tgaggagaca tttctggagc tgaagagttt tagccagagt  600
gaattcccag acatatgcaa agttgatggc attgtgttca accagtgtga gagtgagagt  660
ctacctcagc cctttgatgt tgcatggatg gatgtaggcc actctcataa aatcatcatg  720
agggagcaca agaccaaatg ggtacaagag agctcatcta aggattttgt gtgctacaag  780
gaagggactg ggccgtgttc tgaatcagaa gaaaagactt gcaagaccag tggatcatgc  840
aggggggaca tgcagttttg caaggtagca ggttgtgaac atggggaaga ggcatctgaa  900
gccaaatgta gatgctcact agtgcacaag cccggggaag ttgttgtgtc atatggaggg  960
atgcgtgtca gaccaaagtg ttatggtttc tccagaatga tggcaacact agaggtgaac  1020
ccaccagagc aaagaattgg ccaatgcact ggctgccatc tagaatgcat aaatgggggt  1080
gtgaggctaa ttactctaac tagtgagctc aagtcagcta ctgtctgtgc ttcccacttt  1140
tgtagttctg ctacaagtgg caagaaaagc acggagattc aattccactc agggtcatta  1200
gttgggaaag cagcaattca cgtcaaaggg actttggtgg atggaactga attcacattt  1260
gagggcagtt gcatgttccc agatggttgt gacgcagtgg actgcacatt ctgtcgcgag  1320
ttcctaaaaa atcctcagtg ctaccctgca aagaaatggt tgttcataat tattgccatc  1380
ctccttggat atgcaggcct catgctgctc accaatgttc ttaaggcaat cggggtttgg  1440
ggatcatggg tcatagctcc agtgaagctg atgtttgcca tcataaagaa actgatgaga  1500
tctgtgagct gcttgatggg gaaattaatg gatagggggaa ggcaagtgat tcatgaagaa  1560
ataggggaga atagagaggg caaccaagaa gatgttagaa ttgagattgc aagacccaga  1620
agggtgaggc attggatgta ctcacctgtc atcctggcta ttctagcaat tgggcttgct  1680
gagggctgcg atgagatggt ccatgcagat tcaaaacttg tttcgtgcag gcaagggagc  1740
ggaaatatga aggaatgtgt cacaactggg agggcgcttc ttcctgcggt gaacccagga  1800
caagaggcat gtctgcactt cacggcacct ggaagtccgg actcaaaatg tctcaagatc  1860
aaggttaaga ggatcaacct aaaatgtaag aagtcatcat catattttgt tcctgatgct  1920
cggtccagat gtacgtctgt gaggagatgt cgctgggcag gagactgtca gtctgggtgc  1980
ccctctcatt tcacgtccaa ctccttctct gatgattggg caggtaaaat ggacagggct  2040
ggtctaggat tcagtgggtg ctctgatgga tgtggaggag cagcctgcgg ctgctttaat  2100
gcggcccctt catgcatctt ttggaggaaa tgggtagaga atccacatgg gatcatctgg  2160
aaagtatctc catgtgctgc atgggtccct tcaacagtca tagagctaac aatgccctcg  2220
ggggaagtga ggacattcca ccccatgagc ggcatcccca cacaagtctt caagggtgtg  2280
agtgtgactt acttaggctc agatatggag gtgtctggcc tgactgacct gtgtgagata  2340
gaagagctca agtccaagaa gctggcatta gctccctgca atcaggctgg catgggagtt  2400
gtgggcaagg ttggagagat acagtgcagt agcgaggaaa gcgcccgttc cataaagaaa  2460
gatgggtgta tatggaatgc tgaccttgtg ggcatagagc tacgagtgga tgacgcagtg  2520
tgctattcta agatcactag tgtggaggca gttgcaaact actctgccat acccaccact  2580
attggggggt tgaggtttga gagaagccat gacagccagg gtaaaatatc tggtagcccc  2640
ctagacatta cagccataag agggtctttt tccgttaatt atagaggcct tcgactgagc  2700
ctctcagaaa tcactgctac ttgcacagga gaggtgacga atgtgagtgg gtgttactct  2760
tgcatgacag gcgccaaagt ctccatcaaa ctgcatagca gcaaaaatag cactgcccat  2820
gtaagatgca aaggggatga gaccgcattc agtgtcctgg agggagttca tagctatact  2880
gtcagtctta gctttgacca tgcagtggtc gatgagcagt gccagctgaa ctgtgggggg  2940
catgagagtc aagtgactct aaaaggcaac ctcatcttcc tggatgtccc aaaatttgta  3000
gatggcagct atatgcagac atatcatagt tctgtgccca caggggctaa tatcccaagc  3060
cctacagact ggctgaatgc cttgtttggc aatgggctga gtaggtggat tcttggggta  3120
ataggggttc tactgggggg attggctctc ttcttcttaa ttatgtcctt gttcaaactg  3180
ggaacaaaac agatattccg atcaaggacg aagctggctt ag                    3222

SEQ ID NO: 11          moltype = DNA  length = 738
FEATURE                Location/Qualifiers
misc_feature           1..738
                       note = severe fever thrombocytopenia syndrome virus B-3 NP
                        gene
source                 1..738
```

```
                        mol_type = other DNA
                        organism = unidentified
SEQUENCE: 11
atgtcagagt ggtccaggat tgcagtggag tttggtgagc agcagctcaa tttgactgag  60
cttgaggatt tcgcgagaga gctagcctat gaaggccttg atcctgcctt gataatcaag  120
aagctgaagg agacaggtgg agatgattgg gtgagagata caaagttcat cattgtcttt  180
gccctgaccc gaggcaacaa gatcgtcaag gcatcaggga aaatgtcaaa ctcagggtct  240
aagaggttga tggcacttca agagaaatat ggactggttg agagggcaga aaccaggctc  300
tcaatcactc ctgtgagggt agcacagagc cttcccactt ggacgtgcgc tgcagcagca  360
gccttaaagg agtatctccc agtgggccca gctgtcatga acctgaaggt cgaaaattac  420
cccccagaga tgatgtgcat ggcctttggg tctctgattc caactgcagg ggtatcagaa  480
gccacaacga agaccctgat ggaggcctac tctctgtggc aagatgcctt caccaagact  540
attaatgtga agatgcgtgg agccagcaag acagaggttt acaactcctt cagagatccc  600
ctccatgctg ctgtgaactc tgtcttcttt cccaatgatg ttcgggtgaa gtggctgaag  660
gccaagggaa tcctaggccc agatggggtc cccagcagag ctgctgaggt tgctgctgct  720
gcttacagaa acctgtaa                                                738

SEQ ID NO: 12           moltype = DNA  length = 882
FEATURE                 Location/Qualifiers
misc_feature            1..882
                        note = severe fever thrombocytopenia syndrome virus B-3 NS
                         gene
source                  1..882
                        mol_type = other DNA
                        organism = unidentified
SEQUENCE: 12
atgtcgctga gcaaatgctc caacgttgac ctcaaatctg tagcaatgaa tgccaacact  60
gttaggcttg aaccatctct aggagagtac cccactctta ggaaagacct cgttgaatgc  120
tcttgtagtg tgttgactct atcaatggtc aagaggatgg gcaagatgac caacacagta  180
tggttatttg gcaacccaaa aaatcctctt caccagcttg agcctggact tgagcagctg  240
ttggatatgt actacaagga catgaggtgc tactcccaga gagagctgag tgccctcagg  300
tggcctagtg ggaagccttc tgtatggttc ctacaggcag ctcacatgtt cttttccatc  360
aagaacagct gggcaatgga aaccggtaga gagaactggc ggggcctctt ccacaggata  420
acaaaaggca aaaagtatct tttgaaggg gacatgatat tggattctct tgaagccata  480
gagaagcgaa ggctcagact tgggttacct gagatcctaa taactggact atccccaatt  540
ctggatgtgg ccctcctcca gatagagtca cttgcaaggc taagaggcat gagcttgaac  600
caccacttat tcacttcttc ctcactgcgt aagcctctgt tagattgttg ggacttcttt  660
attcctatcc gcaaaaagaa gacagatggc tcatacagtg ttttggatga ggatgatgag  720
cctggggtcc ttcaaggtta cccatatctg atggcacact atctgaacag gtgcccattc  780
cacaacctca tcagatttga tgaagaactg agaactgcag ccctgaacac catctgggga  840
agagattggc cggccattgg tgacctcccg aaggaggtct aa                     882

SEQ ID NO: 13           moltype = AA  length = 2084
FEATURE                 Location/Qualifiers
REGION                  1..2084
                        note = severe fever thrombocytopenia syndrome virus B-1 L
source                  1..2084
                        mol_type = protein
                        organism = unidentified
SEQUENCE: 13
MDLEVLCGRI NVENGLSLGE PGLYDQIYDR PGLPDLDVTV DATGVTVDIG AVPDSASQLG  60
SSINAGLITI QLSEAYKINH DFTFSGLSKT TDRRLSEVFP ITHDGSDGMT PDVIHTRLDG  120
TIVVVEFSTT RSHNIGGLEA AYRTKIEKYR DPISRRVDIM ENPRVFFGVI VVSSGGVLSN  180
MPLTQDEAEE LMYRFCIANE IYTKARSMDA DIELQKSEEE LEAISRALSF FSLFEPNIER  240
VEGTFPNSEI EMLEQFLSTP ADVDFITKTL KAKEVEAYAD LCDSHYLKPE KTIQERLEIN  300
RCEAIDKTQD LLAGLHARSN KQTSLNRGTV KLPPWLPKPS SESIDIKTDS GFGSLMDHGA  360
YGELWAKCLL DVSLGNVEGV VSDPAKELDI AISDDPEKDT PKEAKITYRR FKPALSSSAR  420
QEFSLQGVEG KKWKRMAANQ KKEKESHETL SPFLDVEDIG DFLTFNNLLA DSRYGDESIQ  480
RAVSILLEKA SAMQDTELTH ALNDSFKRNL SSNVVQWSLW VSCLAQELAS ALKQHCRAGE  540
FIIKKLKFWP IYVIIKPTKS SSHIFYSLGI RKADVTRRLT GRVFSDTIDA GEWELTEFKS  600
LKTCKLTNLV NLPCTMLNSI AFWREKLGVA PWLVRKPCSE LREQVGLTFL ISLEDKSKTE  660
EIITLTRYTQ MEGFVSPPML PKPQKMLGKL DGPLRTKLQV YLLRKHLDCM VRIASQPFSL  720
IPREGRVEWG GTFHAISGRS TNLENMVNSW YIGYYKNKEE STELNALGEM YKKIVEMEED  780
KPSSPEFLGW GDTDSPKKHE FSRSFLRAAC SSLEREIAQR HGRQWKQNLE ERVLREIGTK  840
NILDLASMKA TSNFSKDWEL YSEVQTKEYH RSKLLEKMAT LIEKGVMWYI DAVGQAWKAV  900
LDDGCMRICL FKKNQHGGLR EIYVMDANAR LVQFGVETMA RCVCELSPHE TVANPRLKNS  960
IIENHGLKSA RSLGPGSINI NSSNDARKWN QGHYTTKLAL VLCWFMPAKF HRFIWAAISM  1020
FRRKKMMVDL RFLAHLSSKS ESRSSDPFRE AMTDAFHGNR EVSWMDKGRT YIKTETGMMQ  1080
GILHFTSSLL HSCVQSFYKS YFVSKLKEGY MGESINGVVD VIEGSDDSAI MISIRPKSDM  1140
DEVRSRFFVA NLLHSVKFLN PLFGIYSSEK STVNTVYCVE YNSEFHFHRH LVRPTLRWIA  1200
ASHQISETEA LASRQEDYSN LLTQCLEGGA SFSLTYLIQC AQLLHHYMLL GLCLHPLFGT  1260
FMGMLISDPD PALGFFLMDN PAFAGGAGFR FNLWRACKTT DLGRKYAYYF NEIQGKTKGD  1320
EDYRALDATS GGTLSHSVMV YWGDRKKYQA LLNRMGLPED WVEQIDENPG VLYRRAANKK  1380
ELLLKLAEKV HSPGVTSSLS KGHVVPRVVA AGVYLLSRHC FRFSSSIHGR GSAQKASLIK  1440
LLMMSSVSAM KHGGSLNPNQ ERMLFPQAQE YDRVCTLLEE VEHLTGKFVV RERNIVRSRI  1500
DLFQEPVDLR CKAEDLVSEV WFGLKRTKLG PRLLKEEWDK LRASFAWLST DPSETLRDGP  1560
FLSHVQFRNF IAHVDAKSRS VRLLGAPVKK SGGVTTISQV VRMNFFPGFS LEAEKSLDNQ  1620
ERLESISILK HVLFMVLNGP YTEEYKLEMI IEAFSTLVIP QPSEVIRKSR TMTLCLLSNY  1680
LSSRGGSILD QIERAQSGTL GGFSKPQKTF IRPGGGIGYK GKGVWTGVME DTHVQILIDG  1740
```

-continued

```
DGTSNWLEEI RLSSDARLYD VIESIRRLCD DLGINNRVAS AYRGHCMVRL SGFKIKPASR  1800
TDGCPVRIME RGFRIRELQN PDEVKMRVRG DILNLSVTIQ EGRVMNILSY RPRDTDISES  1860
AAAYLWSNRD LFSFGKKEPS CSWICLKTLD NWAWSHASVL LANDRKTQGI DNKAMGNIFR  1920
DCLEGSLRKQ GLMRSKLTEM VEKNVVPLTT QELVDILEED IDFSDVIAVE LSEGSLDIES  1980
IFDGAPILWS AEVEEFGEGV VAVSYSSKYY HLTLMDQAAI TMCAIMGKEG CRGLLTEKRC  2040
MAAIREQVRP FLIFLQIPED SISWVSDQFC DSRGLDEEST IMWG                   2084

SEQ ID NO: 14           moltype = AA  length = 1073
FEATURE                 Location/Qualifiers
REGION                  1..1073
                        note = severe fever thrombocytopenia syndrome virus B-1 M
source                  1..1073
                        mol_type = protein
                        organism = unidentified
SEQUENCE: 14
MMKVIWFSSL ICLVIQCSGD TGPIICAGPI HSNKSANIPH LLGYSEKICQ IDRLIHVSSW  60
LRNHSQFQGY VGQRGGRSQV SYYPAENSYS RWSGLLSPCD ADWLGMLVVK KAKGSDMIVP  120
GPSYKGKVFF ERPTFDGYVG WGCGSGKSRT ESGELCSSDS GTSSGLLPSD RVLWIGDVAC  180
QPMTPIPEET FLELKSFSQS EFPDICKIDG IVFNQCESES LPQPLDVAWM DVGHSHKIIM  240
REHKTKWVQE SSSKDFVCYK EGTGPCSESE EKTCKTSGSC RGDMQFCKVA GCEHGEEASD  300
AKCRCSLVHK PGEVVVSYGG MRVRPKCYGF SRMMATLEVN PPEQRIGQCT GCHLECINGG  360
VRLITLTSEL KSATVCASHF CSSATSGKKS TEIQFHSGSL VGKTTIHVKG ALVDGTEFTF  420
EGSCMFPDGC DAVDCTFCRE FLKNPQCYPA KKWLFIIIVI LLGYAGLMLL TNVLKAIGVW  480
GSWVIAPVKL MFAIIKKLMR SVSCLMGKLM DRGRQVIHEE IGENREGNQD DVRIEMARPR  540
RVRHWMYSPV ILTILAIGLA EGCDEMVHAD SKLVSCKQGS GNMKECVTTG RALLPAVNPG  600
QEACLHFTAP GSPDSKCLKI KVKRINLKCK KSSSYFVPDA RSRCTSVRRC RWAGDCQSGC  660
PSHFTSNSFS DDWAGKMDRA GLGFSGCSDG CGGAACGCFN AAPSCIFWRK WVENPHGIIW  720
KVSPCAAWVP SAVIELTMPS GEVRTFHPMS GIPTQVFKGV SVTYLGSDME VSGLTDLCEI  780
EELKSKKLAL APCNQAGMGV VGKVGEIQCS SEESARTIKK DGCIWNADLV GIELRVDDAV  840
CYSKITSVEA VANYSAIPTT IGGLRFERSH DSQGKISGSP LDITAIRGSF SVNYRGLRLS  900
LSEVTATCTG EVTNVSGCYS CMTGAKVSIK LHSSKNSTAH VRCKGDETAF SVLVGVHSYT  960
VSLSFDHAVV DEQCQLNCGG HESQVTLKGN LIFLDVPKFV DGSYMQTYHS SVPTGANIPS  1020
PTDWLNALFG NGLSRWILGV IGVLLGGLAL FFLIMSLFKL GTKQVFRSRT KLA         1073

SEQ ID NO: 15           moltype = AA  length = 1073
FEATURE                 Location/Qualifiers
REGION                  1..1073
                        note = severe fever thrombocytopenia syndrome virus B-1 NP
source                  1..1073
                        mol_type = protein
                        organism = unidentified
SEQUENCE: 15
MMKVIWFSSL ICLVIQCSGD TGPIICAGPI HSNKSANIPH LLGYSEKICQ IDRLIHVSSW  60
LRNHSQFQGY VGQRGGRSQV SYYPAENSYS RWSGLLSPCD ADWLGMLVVK KAKGSDMIVP  120
GPSYKGKVFF ERPTFDGYVG WGCGSGKSRT ESGELCSSDS GTSSGLLPSD RVLWIGDVAC  180
QPMTPIPEET FLELKSFSQS EFPDICKIDG IVFNQCESES LPQPLDVAWM DVGHSHKIIM  240
REHKTKWVQE SSSKDFVCYK EGTGPCSESE EKTCKTSGSC RGDMQFCKVA GCEHGEEASD  300
AKCRCSLVHK PGEVVVSYGG MRVRPKCYGF SRMMATLEVN PPEQRIGQCT GCHLECINGG  360
VRLITLTSEL KSATVCASHF CSSATSGKKS TEIQFHSGSL VGKTTIHVKG ALVDGTEFTF  420
EGSCMFPDGC DAVDCTFCRE FLKNPQCYPA KKWLFIIIVI LLGYAGLMLL TNVLKAIGVW  480
GSWVIAPVKL MFAIIKKLMR SVSCLMGKLM DRGRQVIHEE IGENREGNQD DVRIEMARPR  540
RVRHWMYSPV ILTILAIGLA EGCDEMVHAD SKLVSCKQGS GNMKECVTTG RALLPAVNPG  600
QEACLHFTAP GSPDSKCLKI KVKRINLKCK KSSSYFVPDA RSRCTSVRRC RWAGDCQSGC  660
PSHFTSNSFS DDWAGKMDRA GLGFSGCSDG CGGAACGCFN AAPSCIFWRK WVENPHGIIW  720
KVSPCAAWVP SAVIELTMPS GEVRTFHPMS GIPTQVFKGV SVTYLGSDME VSGLTDLCEI  780
EELKSKKLAL APCNQAGMGV VGKVGEIQCS SEESARTIKK DGCIWNADLV GIELRVDDAV  840
CYSKITSVEA VANYSAIPTT IGGLRFERSH DSQGKISGSP LDITAIRGSF SVNYRGLRLS  900
LSEVTATCTG EVTNVSGCYS CMTGAKVSIK LHSSKNSTAH VRCKGDETAF SVLVGVHSYT  960
VSLSFDHAVV DEQCQLNCGG HESQVTLKGN LIFLDVPKFV DGSYMQTYHS SVPTGANIPS  1020
PTDWLNALFG NGLSRWILGV IGVLLGGLAL FFLIMSLFKL GTKQVFRSRT KLA         1073

SEQ ID NO: 16           moltype = AA  length = 293
FEATURE                 Location/Qualifiers
REGION                  1..293
                        note = severe fever thrombocytopenia syndrome virus B-1 NS
source                  1..293
                        mol_type = protein
                        organism = unidentified
SEQUENCE: 16
MSLSKCSNVD LKSVAMNANT VRLEPSLGEY PTLRRDLVEC SCSVLTLSMV KRMGKMTNTV  60
WLFGNPKNPL HQLEPGLEQL LDMYYKDMRC YSQRELSALR WPSGKPSVWF LQAAHMFFSI  120
KNSWAMETGR ENWRGLFHRI TKGKKYLFEG DMILDSLEAI EKRRLRLGLP EILITGLSPI  180
LDVALLQIES LARLRGMSLN HHLFTSSSLR KPLLDCWDFF IPIRKKRTDG SYSILDEDDE  240
LGVLQGYPYL MAHYLNRCPF HNLIRFDEEL RTAALNTIWG RDWPAIGDLP KEV         293

SEQ ID NO: 17           moltype = AA  length = 2084
FEATURE                 Location/Qualifiers
REGION                  1..2084
                        note = severe fever thrombocytopenia syndrome virus B-2 L
```

-continued

```
source                  1..2084
                        mol_type = protein
                        organism = unidentified
SEQUENCE: 17
MNLEVLCGRI NVENGLSLGE PGLYDQIYDR PGLPDLDVTV DATGVTVDIG AVPDSASQLG  60
SSINAGLITI QLSEAYKINH DFTFSGLSKT TDRRLSEVFP ITHDGSDGMT PDVIHTRLDG  120
TIVVVEFSTT RSHNIGGLET AYRTKIEKYR DPISRRVDIM ENPRVFFGVI VVSSGGVLSN  180
MPLTQDEAEE LMYRFCIANE IYTKARSMDA DIELQKSEEE LEAISRALSF FSLFEPNIEK  240
VEGTFPNSEI EMLEQFLSTP ADVDFITKTL KAKEVEAYAD LCDSHYLKPE KTIQERLEIN  300
RCEAIDKTQD LLASLHARSN KQTSLNRGTV KLPPWLPKPS SESIDIKTDS GFGSLMDHGA  360
YGELWAKCLL DVSLGNVEGV ISDPAKELDI AISDDPEKDT PKEAKITYRR FKPALSSSAR  420
QEFSLQGVEG KKWKRMAANQ KKEKESHEAL SPFLDVEDIG DFLTFNNLLA DSRYGDESVQ  480
RAVSILLEKA SAMQNTELTH ALNDSFKRNL SSNVVQWSLW VSCLAQELAS ALKQHCRAGE  540
FIIKKLKFWP IYVIIKPTKS SSHIFYSLGI RKADVTRRLT GRVFSDTIDA GEWELTEFKS  600
LKTCKLTNLV NLPCTMLNSI AFWREKLGVA PWLVRKPCSE LREQVGLTFL ISLEDKSKTE  660
EIITLTRYTQ MEGFVSPPML PKPQKMLGKL DGPLRTKLQV YLLRKHLDCM VRIASQPFSL  720
IPREGRVEWG GTFHAISGRS TNLENMVNSW YIGYYKNKEE STELNALGEM YKKIVEMEED  780
KPSSPEFLGW GDTDSPKKHE FSRSFLRAAC SSLEREIAQR HGRQWKQNLE ERVLREIGTK  840
NILDLASMKA TSNFSKDWEL YSEVQTKEYH RSKLLEKMAT LIEKGVMWYI DAVGQAWKAV  900
LDDGCMRICL FKKNQHGGLR EIYVMDANAR LVQFGVETMA RCVCELSPHE TVANPRLKNS  960
IIENHGLKSA RSLGPGSINI NSSNDAKKWN QGHYTTKLAL VLCWFMPAKF HRFIWAAISM  1020
FRRKKMMVDL RFLAHLSSKS ESRSSDPFRE AMTDAFHGNR EVSWMDKGRT YIKTETGMMQ  1080
GILHFTSSLL HSCVQSFYKS YFVSKLKEGY MGESINGVVD VIEGSDDSAI MISIRPKSDM  1140
DEVRSRFFVA NLLHSVKFLN PLFGIYSSEK STVNTVYCVE YNSEFHFHRH LVRPTLRWIA  1200
ASHQISETEA LASRQEDYSN LLTQCLEGGA SFSLTYLIQC AQLLHHYMLL GLCLHPLFGT  1260
FMGMLISDPD PALGFFLMDN PAFAGGAGFR FNLWRACKTT DLGRKYAYYF NEIQGKTKGD  1320
EDYRALDATS GGTLSHSVMV YWGDRKKYQA LLNRMGLPED WVEQIDENPG VLYRRAANKK  1380
ELLLKLAEKV HSPGVTSSLS KGHVVPRVVA AGVYLLSRHC FRFSSSIHGR GSAQKASLIK  1440
LLMMSSISAM KHGGSLNPNQ ERMLFPQAQE YDRVCTLLEE VEHLTGKFVV RERNIVRSRI  1500
DLFQEPVDLR CKAEDLVSEV WFGLKRTKLG PRLLKEEWDK LRASFAWLST DPSETLRDGP  1560
FLSHVQFRNF IAHVDAKSRS VRLLGAPVKK SGGVTTISQV VRMNFFPGFS LEAEKSLDNQ  1620
ERLESISILK HVLFMVLNGP YTEEYKLEMI IEAFSTLVIP QPSEVIRKSR TMTLCLLSNY  1680
LSSRGGSILD QIERAQSGTL GGFSKPQKTF IRPGGGIGYK GKGVWTGVME DTHVQILIDG  1740
DGTSNWLEEI RLSSDARLYD VIESIRRLCD DLGINNRVAS AYRGHCMVRL SGFKIKPASR  1800
TDGCPVRIME RGFRIRELQN PDEVKMRVRG DILNLSVTIQ EGRVMNILSY RPRDTDISES  1860
AAAYLWSNRD LFSFGKKEPS CSWICLKTLD NWAWSHASVL LANDRKTQGI DNRAMGNIFR  1920
DCLEGSLRKQ GLMRSKLTEM VEKNVVPLTT QELVDILEED IDFSDVIAVE LSEGSLDIES  1980
IFDGAPILWS AEVEEFGEGV VAVSYSSKYY HLTLMDQAAI TMCAIMGKEG CRGLLTEKRC  2040
MAAIREQVRP FLIFLQIPED SISWVSDQFC DSRGLDEEST IMWG                  2084

SEQ ID NO: 18           moltype = AA  length = 1073
FEATURE                 Location/Qualifiers
REGION                  1..1073
                        note = severe fever thrombocytopenia syndrome virus B-2 M
source                  1..1073
                        mol_type = protein
                        organism = unidentified
SEQUENCE: 18
MMKVIWFSSL ICLVIQCSGD TGPIICAGPI HSNKSADIPH LLGYSEKICQ IDRLIHVSSW  60
LRNHSQFQGY VGQRGGRSQV SYFPAENSYS RWSGLLSPCD ADWLGMLVVK KAKGSDMIVP  120
GPSYKGKVFF ERPTFDGYVG WGCGSGKSRT ESGELCSSDS GTSSGLLPSN RVLWIGDVAC  180
QPMTPIPEET FLELKSFSQS EFPDICKIDG IVFNQCESES LPQPFDVAWM DVGHSHKIIM  240
REHKTKWVQE SSSKDFVCYK EGTGPCSESE EKTCKTSGSC RGDMQFCKVA GCEHGEETSE  300
AKCRCSLVHK PGEVVVSYGG MRVRPKCYGF SRMMATLEVN PPEQRIGQCT GCHLECINGG  360
VRIITLTSEL KSATVCASHF CSSATSGKKS TEIQFHSGSL VGKTAIHVKG ALVDGTEFTF  420
EGSCMFPDGC DAVDCTFCRE FLKNPQCYPA KKWLFIIIVI LLGYAGLMLL TNVLKAIGVW  480
GSWVIAPVKL MFAIIKKLMR SVSCLMGKLM DRGRQVIHEE IGENREGNQD DVRIEMARPR  540
RVRHWMYSPV ILTILAIGLA EGCDEMVHAD SKLVSCKQGS GNMKECVTTG RALLPAVNPG  600
QEACLHFTAP GSPDSKCLKI KVKRINLKCK KSSSYFVPDA RSRCTSVRRC RWAGDCQSGC  660
PSHFTSNSFS DDWAGKMDRA GLGFSGCSDG CGGAACGCFN AAPSCIFWRK WVENPHGIIW  720
KVSPCAAWVP SAVIELTMPS GEVRTFHPMS GIPTQVFKGV SVTYLGSDME VSGLTDLCEI  780
EELKSKKLAL APCNQAGMGV VGKVGEIQCS SEESARTIKK DGCIWNADLV GIELRVDDAV  840
CYSKITSVEA VANYSAIPTT IGGLRFERSH DSQGKISGSP LDITAIRGSF SVNYRGLRLS  900
LSEITATCTG EVTNVSGCYS CMTGAKVSIK LHSSKNSTAH VRCKGDETAF SVLEGVHSYT  960
VSLSFDHAVV DEQCQLNCGG HESQVTLKGN LIFLDVPKFV DGSYMQTYHS SVPTGANIPS  1020
PTDWLNALFG NGLSRWILGV IGVLLGGLAL FFLIMSLFKL GTKQVFRSRT KLA         1073

SEQ ID NO: 19           moltype = AA  length = 245
FEATURE                 Location/Qualifiers
REGION                  1..245
                        note = severe fever thrombocytopenia syndrome virus B-2 NP
source                  1..245
                        mol_type = protein
                        organism = unidentified
SEQUENCE: 19
MSEWSRIAVE FGEQQLNLTE LEDFARELAY EGLDPALIIK KLKETGGDDW VRDTKFIIVF  60
ALTRGNKIVK ASGKMSNSGS KRLMALQEKY GLVERAETRL SITPVRVAQS LPTWTCAAAA  120
ALKEYLPVGP AVMNLKVENY PPEMMCMAFG SLIPTAGVSE ATTKTLMEAY SLWQDAFTKT  180
INVKMRGASK TEVYNSFRDP LHAAVNSVFF PNDVRVKWLK AKGILGPDGV PSRAAEVAAA  240
```

```
AYRNL                                                             245

SEQ ID NO: 20           moltype = AA  length = 293
FEATURE                 Location/Qualifiers
REGION                  1..293
                        note = severe fever thrombocytopenia syndrome virus B-2 NS
source                  1..293
                        mol_type = protein
                        organism = unidentified
SEQUENCE: 20
MSLSKCSNVD LKSVAMNANT VRLEPSLGEY PTLRRDLVEC SCSVLTLSMV KRMGKMTNTV  60
WLFGNPKNPL HQLEPGLEQL LDMYYKDMRC YSQRELSALR WPSGKPSVWF LQAAHMFFSI  120
KNSWAMETGR ENWRGLFHRI TKGQKYLFEG DMILDSLEAI EKRRLRLGLP EILITGLSPI  180
LDVALLQIES LARLRGMSLN HHLFTSSSLR KPLLDCWDFF IPIRKKKTDG SYSVLDEDDE  240
PGILQGYPYL MAHYLNRCPF HNLIRFDEEL RTAALNTIWG RDWPAIGDLP KEV         293

SEQ ID NO: 21           moltype = AA  length = 2084
FEATURE                 Location/Qualifiers
REGION                  1..2084
                        note = severe fever thrombocytopenia syndrome virus B-3 L
source                  1..2084
                        mol_type = protein
                        organism = unidentified
SEQUENCE: 21
MNLEVLCGRI NVENGLSLGE PGLYDQIYDR PGLPDLDVTV DAIGVTVDIG AVPDSASQLG  60
SSINAGLITI QLSEAYKINH DFTFSGLSKT TDRRLSEVFP ITHDGSDGMT PDVIHTRLDG  120
TIVVVEFSTT RSHNIGGLEA AYRTKIEKYR DPISRRVDIM ENPRVFFGVI VVSSGGVLSN  180
MPLTQDEAEE LMYRFCIANE IYTKARSMDA DIELQKSEEE LEAISRALSF FSLFEPNIER  240
VEGTFPNSEI EMLEQFLSTP ADVDFITKTL KAKEVEAYAD LCDSHYLKPE KTIQERLEIN  300
RCEAIDKTQD LLASLHARSN KQTSLNRGTV KLPPWLPKPS SESIDIKTDS GFGSLMDHGT  360
YGELWAKCLL DVSLGNVEGV VSDPAKELDI AISDDPEKDT PKEAKITYRR FKPALSSSAR  420
QEFSLQGVEG KKWKRMAANQ KKEKESHETL SPFLDVEDIG DFLTFNNLLA DSRYGDESVQ  480
RAVSILLEKA SAMQDTELTH ALNDSFKRNL SSNVVQWSLW VSCLAQELAS ALKQHCRAGE  540
FIIKKLKFWP IYVIIKPTKS SSHIFYSLGI RKADVTRRLT GRVFSDTIDA GEWELTEFKS  600
LKTCKLTNLV NLPCTMLNSI AFWREKLGVA PWLVRKPCSE LREQVGLTFL ISLEDKSKTE  660
EIITLTRYTQ MEGFVSPPML PKPQKMLGKL DGPLRTKLQV YLLRKHLDCM VRIASQPFSL  720
IPREGRVEWG GTFHAISGRS TNLENMVNSW YIGYYKNKEE STELNALGEM YKKIVEMEED  780
KPSSPKFLGW GDTDSPKKHE FSRSFLRAAC SSLEREIAQR HGRQWKQNLE ERVLREIGTK  840
NILDLASMKA TSNFSKDWEL YSEVQTKEYH RSKLLEKMAT LIEKGVMWYI DAVGQAWKAV  900
LDDGCMRICL FKKNQHGGLR EIYVMDANAR LVQFGVETMA RCVCELSPHE TVANPRLKNS  960
IIENHGLKSA RSLGPGSINI NSSNDAKKWN QGHYTTKLAL VLCWFMPAKF HRFIWAAISM  1020
FRRKKMMVDL RFLAHLSSKS ESRSSDPFRE AMTDAFHGNR EVSWMDKGRT YIKTETGMMQ  1080
GILHFTSSLL HSCVQSFYKS YFVSKLKEGY MGESISGVVD VIEGSDDSAI MISIRPKSDM  1140
DEVRSRFFVA NLLHSVKFLN PLFGIYSSEK STVNTVYCVE YNSEFHFHRH LVRPTLRWIA  1200
ASHQISETEA LASRQEDYSN LLTQCLEGGA SFSLTYLIQC AQLLHHYMLL GLCLHPLFGT  1260
FMGMLISDPD PALGFFLMDN PAFAGGAGFR FNLWRACKTT DLGRKYAYYF NEIQGKTKGD  1320
EDYRALDATS GGTLSHSVMV YWGDRKKYQA LLNRMGLPED WVEQIDENPG VLYRRAANKK  1380
ELLLKLAEKV HSPGVTSSLS KGHVVPRVVA AGVYLLSRHC FRFSSSIHGR GSAQKASLIK  1440
LLMMSSISAM KHGGSLNPNQ ERMLFPQAQE YDRVCTLLEE VEHLTGKFVV RERNIVRSRI  1500
DLFQEPVDLR CKAEDLVSEV WFGLKRTKLG PRLLKEEWDK LRASFAWLST DPSETLRDGP  1560
FLSHVQFRNF IAHVDAKSRS VRLLGAPVKK SGGVTTISQV VRMNFFPGFS LEAEKSLDNQ  1620
ERLESISILK HVLFMVLNGP YTEEYKLDMI IEAFSTLVIP QPSEVIRKSR TMTLCLLSNY  1680
LSSRGGSILD QIERAQSGTL GGFSKPQKTF IRPGGGIGYK GKGVWTGVME DTHVQILIDG  1740
DGTSNWLEEI RLSSDARLYD VIESIRRLCD DLGINNRVAS AYRGHCMVRL SGFKIKPASR  1800
TDGCPVRIME RGFRIRELQN PDEVKMRVRG DILNLSVTIQ EGRVMNILSY RPRDTDISES  1860
AAAYLWSNRD LFSFGKKEPS CSWICLKTLD NWAWSHASVL LANDRKTQGI DNRAMGNIFR  1920
DCLEGSLRKQ GLMRSKLTEM VEKNVVPLTT QELVDILEED IDFSDVIAVE LSEGSLDIES  1980
IFDGAPILWS AEVEEFGEGV VAVSYSSKYY HLTLMDQAAI TMCAIMGKEG CRGLLTEKRC  2040
MAAIREQVRP FLIFLQIPED SISWVSDQFC DSRGLDEEST IMWG                  2084

SEQ ID NO: 22           moltype = AA  length = 1073
FEATURE                 Location/Qualifiers
REGION                  1..1073
                        note = severe fever thrombocytopenia syndrome virus B-3 M
source                  1..1073
                        mol_type = protein
                        organism = unidentified
SEQUENCE: 22
MMKVIWFSSL ICLVIQCSGD TGPIICAGPI HSNKSANIPH LLGYSEKICQ IDRLIHVSSW  60
LRNHSQFQGY VGQRGGRSQV SYYPAENSYS RWSGLLSPCD ADWLGMLVVK KAKGSDMIVP  120
GPSYKGKVFF ERPTFDGYVG WGCGSGKSRT ESGELCSSDS GTSSGLLPSN RVLWIGDVAC  180
QPMTPIPEET FLELKSFSQS EFPDICKVDG IVFNQCESES LPQPFDVAWM DVGHSHKIIM  240
REHKTKWVQE SSSKDFVCYK EGTGPCSESE EKTCKTSGSC RGDMQFCKVA GCEHGEEASE  300
AKCRCSLVHK PGEVVVSYGG MRVRPKCYGF SRMMATLEVN PPEQRIGQCT GCHLECINGG  360
VRLITLTSEL KSATVCASHF CSSATSGKKS TEIQFHSGSL VGKAAIHVKG TLVDGTEFTF  420
EGSCMFPDGC DAVDCTFCRE FLKNPQCYPA KKWLFIIIAI LLGYAGLMLL TNVLKAIGVW  480
GSWVIAPVKL MFAIIKKLMR SVSCLMGKLM DRGRQVIHEE IGENREGNQE DVRIEIARPR  540
RVRHWMYSPV ILAILAIGLA EGCDEMVHAD SKLVSCRQGS GNMKECVTTG RALLPAVNPG  600
QEACLHFTAP GSPDSKCLKI KVKRINLKCK KSSSYFVPDA RSRCTSVRRC RWAGDCQSGC  660
```

-continued

```
PSHFTSNSFS DDWAGKMDRA GLGFSGCSDG CGGAACGCFN AAPSCIFWRK WVENPHGIIW  720
KVSPCAAWVP STVIELTMPS GEVRTFHPMS GIPTQVFKGV SVTYLGSDME VSGLTDLCEI  780
EELKSKKLAL APCNQAGMGV VGKVGEIQCS SEESARSIKK DGCIWNADLV GIELRVDDAV  840
CYSKITSVEA VANYSAIPTT IGGLRFERSH DSQGKISGSP LDITAIRGSF SVNYRGLRLS  900
LSEITATCTG EVTNVSGCYS CMTGAKVSIK LHSSKNSTAH VRCKGDETAF SVLEGVHSYT  960
VSLSFDHAVV DEQCQLNCGG HESQVTLKGN LIFLDVPKFV DGSYMQTYHS SVPTGANIPS  1020
PTDWLNALFG NGLSRWILGV IGVLLGGLAL FFLIMSLFKL GTKQIFRSRT KLA         1073

SEQ ID NO: 23          moltype = AA  length = 245
FEATURE                Location/Qualifiers
REGION                 1..245
                       note = severe fever thrombocytopenia syndrome virus B-3 NP
source                 1..245
                       mol_type = protein
                       organism = unidentified
SEQUENCE: 23
MSEWSRIAVE FGEQQLNLTE LEDFARELAY EGLDPALIIK KLKETGGDDW VRDTKFIIVF  60
ALTRGNKIVK ASGKMSNSGS KRLMALQEKY GLVERAETRL SITPVRVAQS LPTWTCAAAA  120
ALKEYLPVGP AVMNLKVENY PPEMMCMAFG SLIPTAGVSE ATTKTLMEAY SLWQDAFTKT  180
INVKMRGASK TEVYNSFRDP LHAAVNSVFF PNDVRVKWLK AKGILGPDGV PSRAAEVAAA  240
AYRNL                                                            245

SEQ ID NO: 24          moltype = AA  length = 293
FEATURE                Location/Qualifiers
REGION                 1..293
                       note = severe fever thrombocytopenia syndrome virus B-3 NS
source                 1..293
                       mol_type = protein
                       organism = unidentified
SEQUENCE: 24
MSLSKCSNVD LKSVAMNANT VRLEPSLGEY PTLRKDLVEC SCSVLTLSMV KRMGKMTNTV  60
WLFGNPKNPL HQLEPGLEQL LDMYYKDMRC YSQRELSALR WPSGKPSVWF LQAAHMFFSI  120
KNSWAMETGR ENWRGLFHRI TKGKKYLFEG DMILDSLEAI EKRRLRLGLP EILITGLSPI  180
LDVALLQIES LARLRGMSLN HHLFTSSSLR KPLLDCWDFF IPIRKKKTDG SYSVLDEDDE  240
PGVLQGYPYL MAHYLNRCPF HNLIRFDEEL RTAALNTIWG RDWPAIGDLP KEV         293
```

SEVERE FEVER WITH THROMBOCYTOPENIA SYNDROME VIRUS

CROSS REFERENCE TO RELATED APPLICATIONS

This application is a Continuation Application of U.S. application Ser. No. 17/050,602 filed Oct. 26, 2020 which is a National Stage Application of International Application No. PCT/KR2019/004857 filed Apr. 23, 2019, claiming priority based on Korean Patent Application No. 10-2018-0047865 filed Apr. 25, 2018, the entire disclosures of which are incorporated herein by reference.

INCORPORATION BY REFERENCE OF SEQUENCE LISTING

The content of the electronically submitted sequence listing, file name: Q288727_sequence listing as filed.XML; size: 76,505 bytes; and date of creation: Jul. 1, 2023, filed herewith, is incorporated herein by reference in its entirety.

TECHNICAL FIELD

The present disclosure relates to a novel genotype of severe fever with thrombocytopenia syndrome virus and use thereof as an immunogenic composition.

BACKGROUND ART

A severe fever with thrombocytopenia syndrome (SFTS) is accompanied by symptoms such as high fever, vomiting, diarrhea, thrombocytopenia, leukopenia and multiple organ failure, and is a serious disease with a mortality rate of 6% to 30% (Yu X J et al., N. Engl. J. Med. 2011; 364:1523-32; Ding F et al Clin Infect Dis 2013; 56: 1682-3).

A causative pathogen of SFTS is SFTSV (severe fever thrombocytopenia syndrome virus), which belongs to Bunyaviridae family. Bunyaviridae family is a negative-strand RNA virus containing three segments. Bunyaviridae family includes five genera including *Orthobunyavirus, Hantavirus, Nairovirus, Phlebovirus* and *Tospovirus*. SFTSV belongs to the *Phlebovirus* genus which includes Rift valley fever virus. SFTSV was first reported in China in 2011 (Yu X J et al. ibid), and is a new variant virus that continues to outbreak not only in China, but also in Korea and Japan. SFTSV is a ball-shaped virus with a diameter of 80 nm to 100 nm. This virus carries three genes: a large (L) segment as a single-stranded negative sense RNA segment, a medium (M) segment, and a small (S) segment (NP, NS).

The SFTS virus is known to spread via Haemaphysalis longicornis as a vector thereof, which spreads widely in Korea as well (Chae J S et al. J Vet Sci 2008; 9: 285-93; Kim C M et al. Appl Environ Microbiol 2006; 72: 5766-76). Seroconversion and viraemia of the SFTS virus have been found in domestic animals such as goats, sheep, cattle, pigs and dogs. It is believed that these animals act as intermediate vectors thereof in the area where SFTS virus spreads (Zhao L et al. Emerg Infect Dis 2013; 18: 963-5; Niu G et al. Emerg Infect Dis 2013; 19: 756-63). SFTSV is detected in the blood of patients, and the concentration of SFTSV is very high in blood of severely ill patients. Thus, human-to-human transmission thereof is possible via the blood (Tang X, Wu W, Wang H, et al. J Infect Dis 2013; 207: 736-739. ).

Antiviral agents for SFTSV have not been developed yet, and thus SFTS treatment is based on conservative therapy for organ failure such as blood transfusion and renal replacement therapy. In China, ribavirin infusion has been introduced into the treatment guidelines since 2012. However, there was no difference in the mortality rate between the ribavirin-treated group and the non-administered group in the recently published treatment results. Therefore, a vaccine against SFTSV is required, but such a vaccine has not been developed yet.

DISCLOSURE

Technical Purpose

A purpose of the present disclosure is to provide a novel genotype of severe fever with thrombocytopenia syndrome virus and an immunogenic composition containing the same.

Technical Solution

To achieve the purpose, the present disclosure provides a novel severe fever with thrombocytopenia syndrome virus.

Further, the present disclosure provides an immunogenic composition for prevention or treatment of the severe fever with thrombocytopenia syndrome.

Further, the present disclosure provides antibodies against the severe fever with thrombocytopenia syndrome virus or an antigen thereof.

Further, the present disclosure provides a diagnostic kit for the severe fever with thrombocytopenia syndrome virus.

Further, the present disclosure provides a method to detect the severe fever with thrombocytopenia syndrome virus antibody.

Further, the present disclosure provides a method for producing antiserum against the severe fever with thrombocytopenia syndrome virus.

In addition, the present disclosure provides a method to provide information regarding diagnosis of the severe fever with thrombocytopenia syndrome.

Advantageous Effects

The severe fever with thrombocytopenia syndrome virus according to the present disclosure is genetically different from the conventional thrombocytopenia virus and is a novel virus as systematically subdivided from a B genotype. Thus, the novel virus according to the present disclosure may be usefully used as vaccines with excellent cross immunogenicity against SFTSV, due to characteristics of a vaccine that only a specific genotype virus exhibits limited protective ability.

MODES OF THE INVENTION

Figure 1:
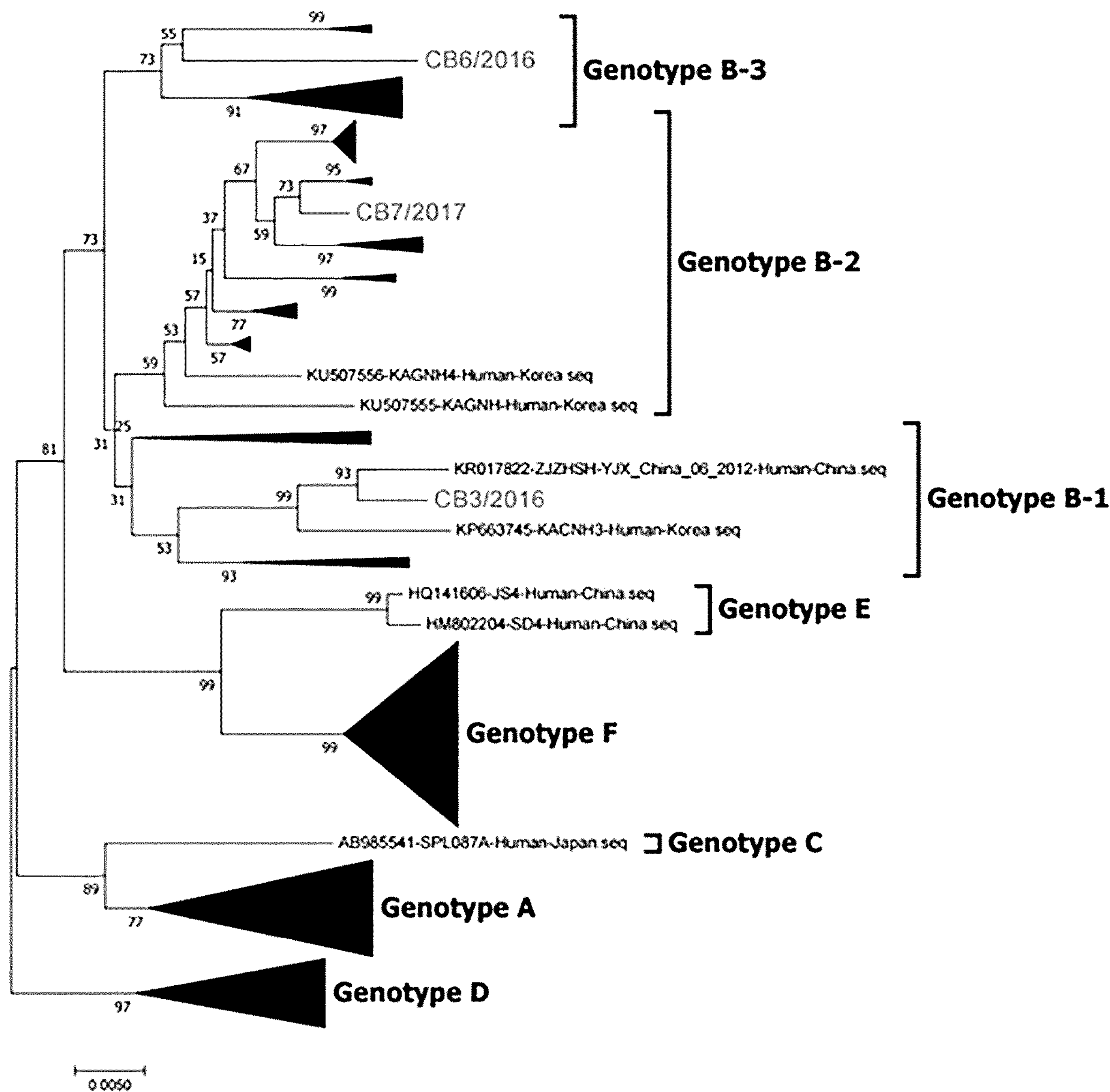
FIG. 1 is a phylogenetic tree showing three novel viruses according to the present disclosure and SFTSV L gene isolated from China, Japan, and Korea.
Figure 2:
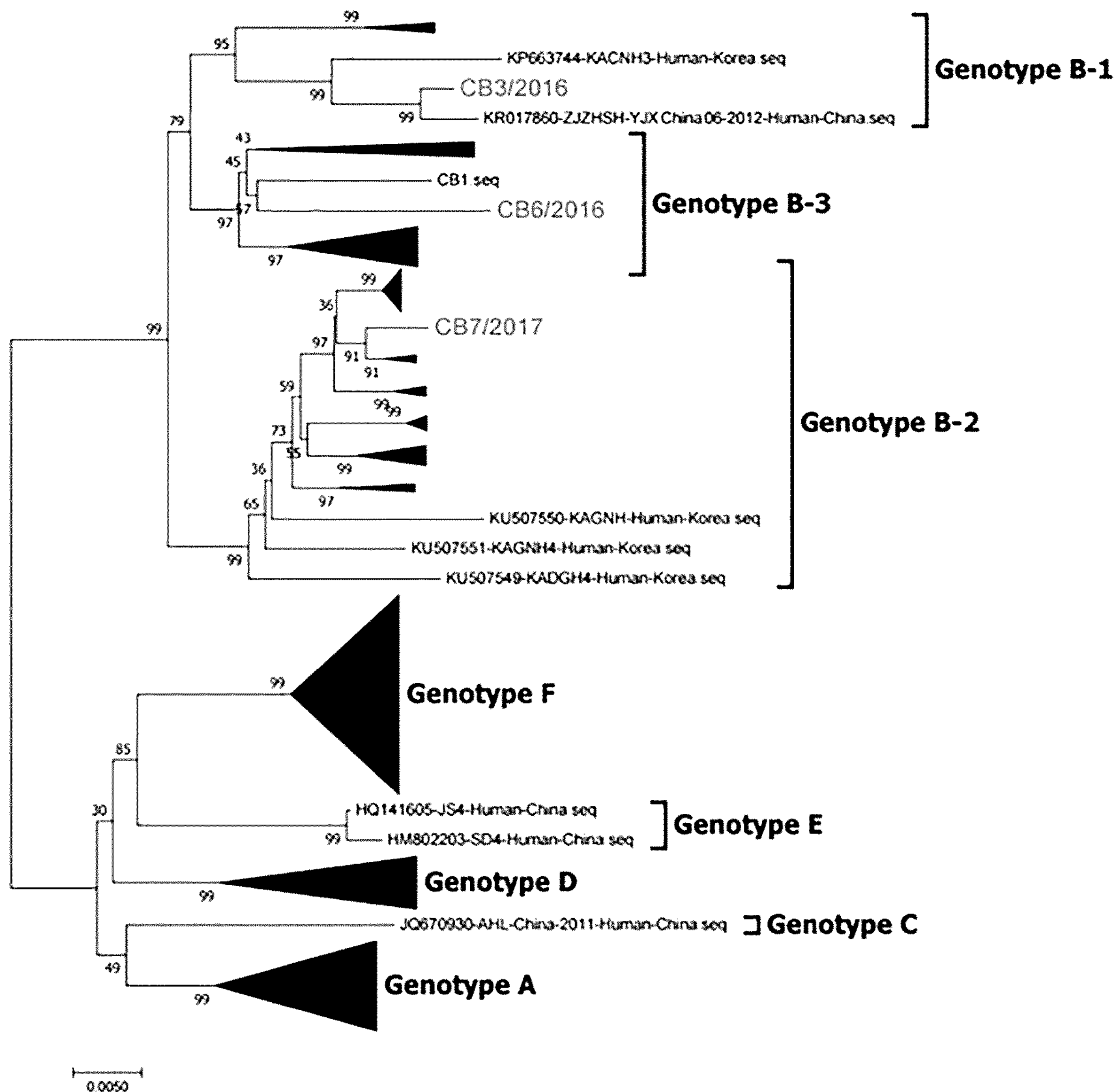
FIG. 2 is a phylogenetic tree showing the three novel viruses according to the present disclosure and SFTSV M gene isolated from China, Japan, and Korea.
Figure 3:
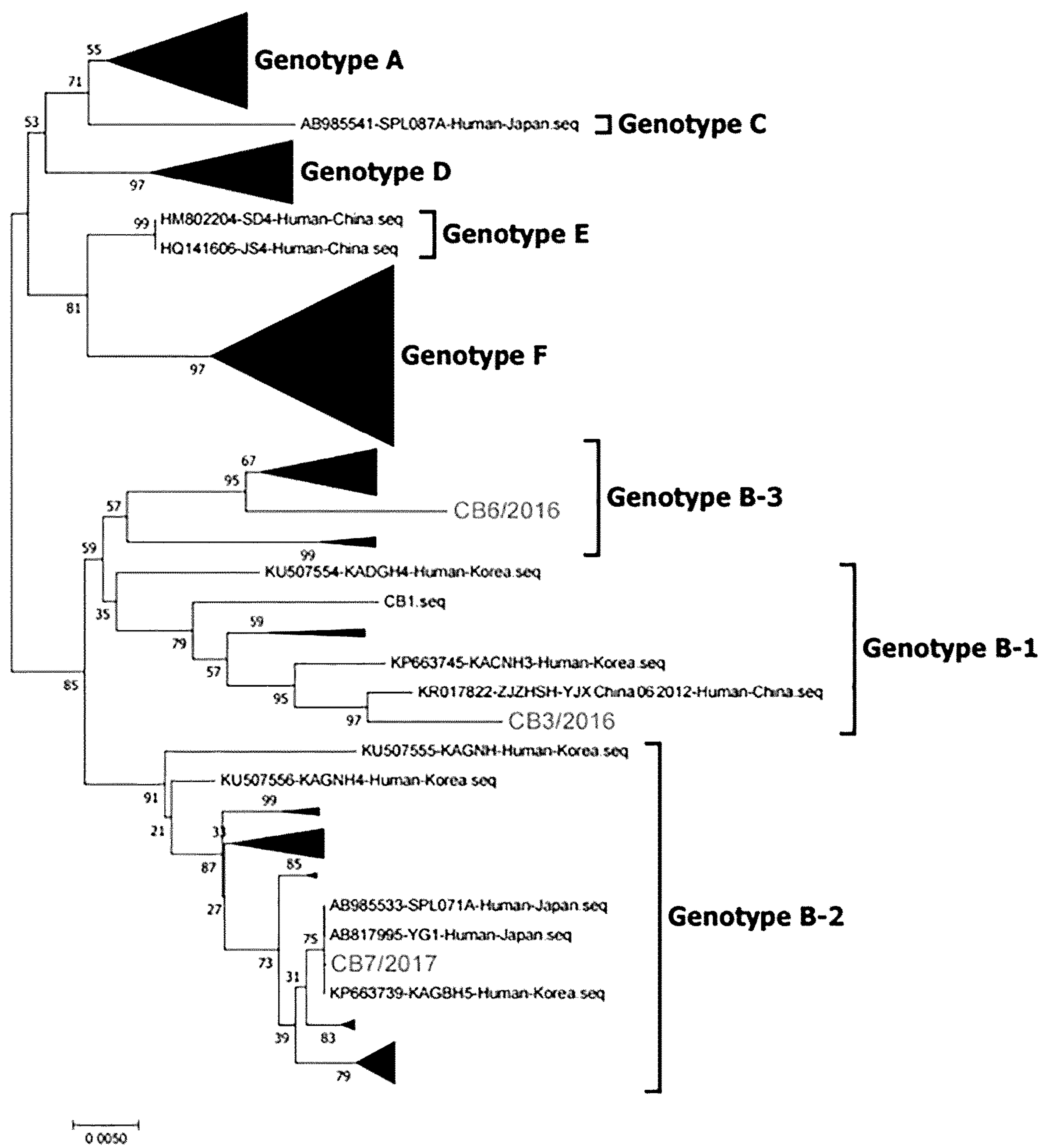
FIG. 3 is a phylogenetic tree showing the three novel viruses according to the present disclosure and SFTSV S (NP) gene isolated from China, Japan, and Korea.
Figure 4:
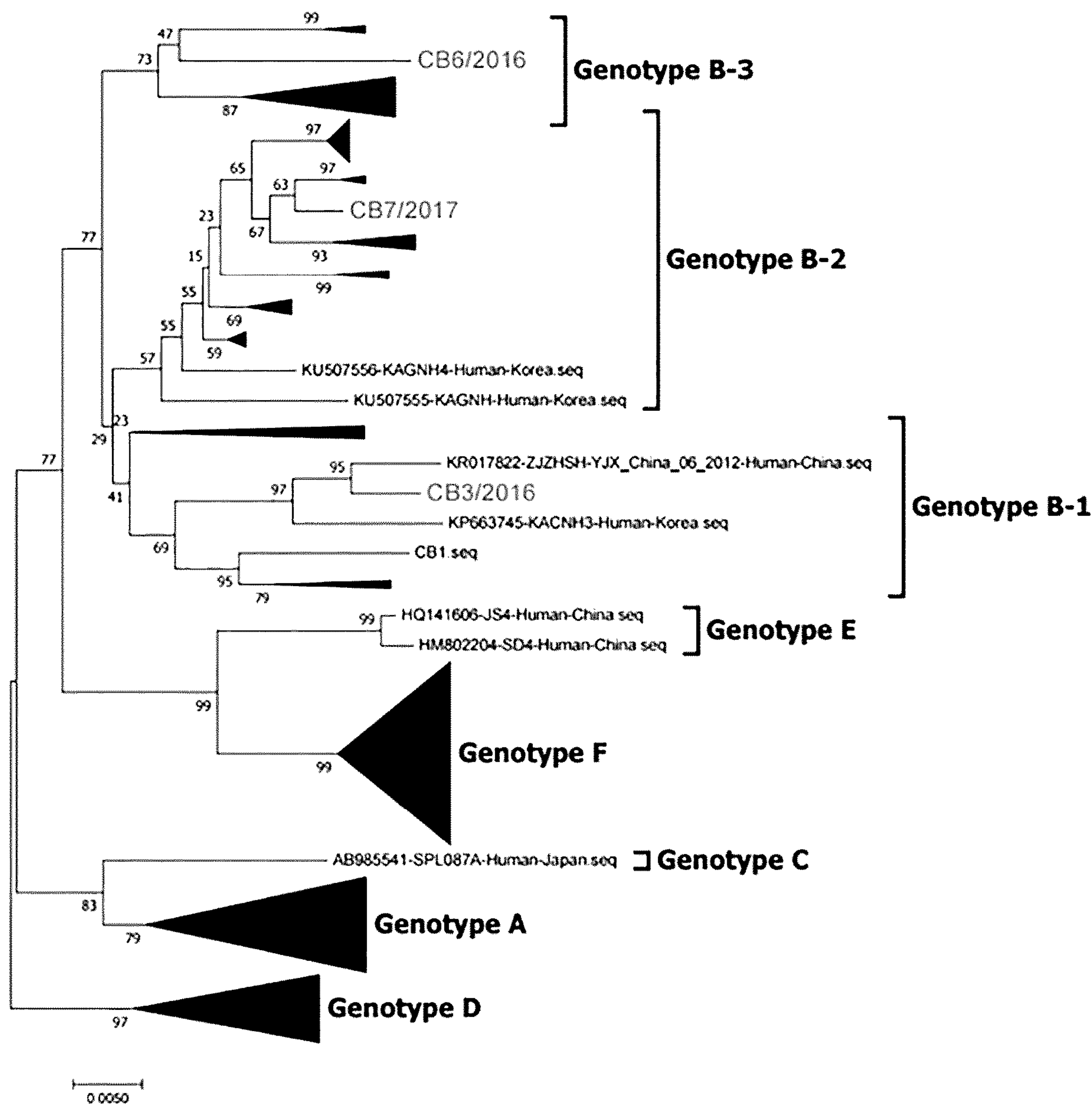
FIG. 4 is a phylogenetic tree showing the three novel viruses according to the present disclosure and SFTSV S (NS) gene isolated from China, Japan, and Korea.

Hereinafter, the present disclosure will be described in detail based on implementations according to the present disclosure with reference to the accompanying drawings. However, the following implementations are presented as only examples of the present disclosure. When it is determined that detailed description of a well-known component or configuration may unnecessarily obscure the gist of the present disclosure, the detailed description may be omitted. The implementations do not limit the present disclosure. The present disclosure may be variously modified and applied within the scope interpreted based on the claims to be described later.

Further, terms (terminologies) used in this specification are used to properly describe preferred Example of the present disclosure, and may vary according to a user's or operator's intention or a practice of the field to which the present disclosure belongs. Accordingly, definitions of these terms should be made based on contents throughout the present specification. It will be further understood that the terms "comprises", "comprising", "includes", and "including", "containing" and "contains", etc. when used in this specification, specify the presence of the stated elements, and/or components, but do not preclude the presence or addition of one or more other elements, components, and/or portions thereof.

In one aspect, the present disclosure relates to the severe fever with thrombocytopenia syndrome virus (SFTSV) in which a 1447-th amino acid of a protein expressed in ORF (6255 bp) of an L gene thereof is valine or a 1913-rd amino acid thereof is lysine, wherein a 83-rd amino acid of a protein expressed in ORF (3222 bp) of an M gene thereof is tyrosine, or a 404-th amino acid thereof is threonine or a 904-th amino acid thereof is valine. In one Example of the present disclosure, this virus was named B-1 (CB3).

In one implementation, the severe fever with thrombocytopenia syndrome virus belongs to genotype B-1 and may be a virus in which isoleucine as a 1447-th amino acid of a protein expressed in ORF (6255 bp) of an L gene of a virus conventionally classified as a genotype B is substituted with valine, and arginine as a 1913-rd amino acid thereof is substituted (SEQ ID NO: 13) with lysine, and isoleucine as a 904-th amino acid of an M gene thereof is substituted (SEQ ID NO: 14) with valine.

In one implementation, the severe fever with thrombocytopenia syndrome virus may contain an L gene containing a base sequence represented by SEQ ID NO: 1, an M gene containing a base sequence represented by SEQ ID NO: 2, and an S gene containing NP containing a base sequence represented by SEQ ID NO: 3 and NS containing a base sequence represented by SEQ ID NO: 4.

In one implementation, the severe fever with thrombocytopenia syndrome virus may contain an amino acid sequence represented by SEQ ID NO: 13 expressed in ORF (6255 bp) of an L gene, an amino acid sequence represented by SEQ ID NO: 14 expressed in ORF (3222 bp) of an M gene, and an amino acid sequence represented by SEQ ID NO: 15 expressed in ORF of an NP gene, and an amino acid sequence represented by SEQ ID NO: 16 expressed in ORF of an NS gene.

In one aspect, the present disclosure relates to a severe fever with thrombocytopenia syndrome virus in which a 1447-th amino acid of a protein expressed in ORF (6255 bp) of an L gene thereof is isoleucine or a 1913-rd amino acid thereof is arginine, wherein a 83-rd amino acid of a protein expressed in ORF (3222 bp) of an M gene is phenylalanine, a 404-th amino acid thereof is threonine or a 904-th amino acid thereof is isoleucine. In one Example of the present disclosure, the virus was named B-2 (CB4).

In one implementation, the severe fever with thrombocytopenia syndrome virus belongs to genotype B-2, and may be a virus in which tyrosine as an 83-rd amino acid of an M gene of a virus conventionally classified as a genotype B has been replaced with phenylalanine.

In one implementation, the severe fever with thrombocytopenia syndrome virus may contain an L gene containing a base sequence represented by SEQ ID NO: 5, an M gene containing a base sequence represented by SEQ ID NO: 6, and an S gene containing a NP containing a base sequence represented by SEQ ID NO: 7 and a NS containing a base sequence represented by SEQ ID NO: 8.

In one implementation, the severe fever with thrombocytopenia syndrome virus may contain an amino acid sequence represented by SEQ ID NO: 17 expressed in ORF of an L gene, an amino acid sequence represented by SEQ ID NO: 18 expressed in ORF of an M gene, an amino acid sequence represented by SEQ ID NO: 19 expressed in ORF of an NP gene and an amino acid sequence represented by SEQ ID NO: 20 expressed in ORF of an NS gene.

In one aspect, the present disclosure relates to a severe fever with thrombocytopenia syndrome virus in which a 1447-th amino acid of a protein expressed in ORF (6255 bp) of an L gene thereof is isoleucine or a 1913-rd amino acid thereof is arginine, wherein a 83-rd amino acid of a protein expressed in ORF (3222 bp) of an M gene thereof is tyrosine, a 404-th amino acid thereof is alanine or a 904-th amino acid thereof is isoleucine. In one Example of the present disclosure, the virus was named B-3 (CB1).

In one implementation, the severe fever with thrombocytopenia syndrome virus belongs to genotype B-3, and may be a virus in which threonine as a 404-th amino acid of an M gene of a virus conventionally classified as a genotype B is substituted with alanine.

In one implementation, the severe fever with thrombocytopenia syndrome virus may contain an L gene containing a base sequence represented by SEQ ID NO: 9, an M gene containing a base sequence represented by SEQ ID NO: 10, and an S gene containing NP containing a base sequence represented by SEQ ID NO: 11 and NS containing a base sequence represented by SEQ ID NO: 12.

In one implementation, the severe fever with thrombocytopenia syndrome virus may contain an amino acid sequence represented by SEQ ID NO: 21 expressed in ORF of an L gene, an amino acid sequence represented by SEQ ID NO: 22 expressed in ORF of an M gene, an amino acid sequence represented by SEQ ID NO: 23 expressed in ORF of an NP gene, and an amino acid sequence represented by SEQ ID NO: 24 expressed in ORF of an NS gene.

In one example of the present disclosure, it was revealed based on a result of genetic analysis of the severe fever with thrombocytopenia syndrome virus as isolated that a gene sequence thereof was different from that of the severe fever with thrombocytopenia syndrome virus as previously known. It was revealed based on a result of systematically classifying the severe fever with thrombocytopenia syndrome virus according to the present disclosure that a genotype thereof is subdivided into at least three genotypes other than a single B genotype group as previously known.

The term "substitution" as used in the present disclosure refers to replacement of one or more amino acids or nucleotides by other amino acids or nucleotides, respectively.

The severe fever with thrombocytopenia syndrome virus according to the present disclosure is a negative single-stranded RNA virus and belongs to Bunyaviridae family and to *phlebovirus* genus. The severe fever with thrombocytopenia syndrome virus according to the present disclosure is a spherical virus with a diameter of 80 nm to 100 nm and spreads via *Haemaphysalis longicornis* as a vector thereof. A genome thereof includes a large (L) segment, a medium (M) segment, and a small (S) segment and codes six proteins including RNA dependent RNA polymerase (RdRp), glycoprotein precursor (M), glycoprotein N (Gn), glycoprotein C (Gc), nucleocapsid protein (NP), and non-structural protein (NS). In a negative or antisense strand (sense encoding a viral protein or antisense against a positive strand), a protein or gene is encoded as antisense. For expression of a gene into a protein, a sense or positive strand RNA is generated, and then translation therefrom is performed such that the protein is produced.

In one aspect, the present disclosure relates to an immunogenic composition for prevention or treatment of a severe fever with thrombocytopenia syndrome, the composition containing the severe fever with thrombocytopenia syndrome virus or an antigen thereof as an active ingredient.

In one implementation, the immunogenic composition according to the present disclosure may contain an inactivated severe fever with thrombocytopenia syndrome virus and a pharmaceutically acceptable carrier or adjuvant.

In one implementation, the immunogenic composition may be a vaccine composition, wherein a form thereof may be selected from the group consisting of live vaccine, killed vaccine, subunit vaccine produced using a gene of an attenuated severe fever with thrombocytopenia syndrome virus, vector vaccine, chimeric vaccine, DNA vaccine, and RNA vaccine.

In one implementation, the immunogenic composition may contain, as an active ingredient, a severe fever with thrombocytopenia syndrome virus containing an L gene containing a base sequence represented by SEQ ID NO: 1, an M gene containing a base sequence represented by SEQ ID NO: 2, and an S gene containing a base sequence represented by SEQ ID NO: 3; a severe fever with thrombocytopenia syndrome virus containing an L gene containing a base sequence represented by SEQ ID NO: 4, an M gene containing a base sequence represented by SEQ ID NO: 5, and an S gene containing a base sequence represented by SEQ ID NO: 6; and a severe fever with thrombocytopenia syndrome virus containing an L gene containing a base sequence represented by SEQ ID NO: 7, an M gene containing a base sequence represented by SEQ ID NO: 8, and an S gene containing a base sequence represented by SEQ ID NO: 9; or antigens thereof.

For preparation of the immunogenic composition (i.e., a vaccine) according to the present disclosure, the virus or an antigen thereof according to the present disclosure is transformed into a physiologically acceptable form. This may be done based on experiences of preparing a vaccine used for vaccination against influenza (disclosed by Stickl, H. et al. [1974] Dtsch. med. Wschr. 99, 2386-2392). For the preparation of vaccine injections, for example, virus particles are lyophilized in 100 ml of phosphate-buffered saline (PBS) under the presence of 1% human albumin and 2% peptone in ampoules, preferably in glass ampoules. Alternatively, vaccine injections may be produced by sequential freeze-drying of the virus in the formulation. This formulation may contain additional additives such as mannitol, dextran, sugar, glycine, lactose or polyvinylpyrrolidone or antioxidants or inert gases, stabilizers or other adjuvants such as recombinant proteins suitable for in vivo administration (e.g. human serum albumin). The glass ampoule may then be sealed and stored at a temperature between 4° C. and room temperature for several months. However, unless otherwise required, the ampoules may preferably be stored below −20° C.

For vaccination or treatment, the lyophilisate may be dissolved in 0.1 ml to 0.5 ml of an aqueous solution, preferably physiological saline or tris buffer, and then may be administered to a subject systemically or locally, i.e. in parenteral, subcutaneous, intramuscular manner or via other routes of administration known to those skilled in the art. A dosage form, dosage and frequency of administration thereof may be optimized by a person skilled in the art in a known manner. However, most commonly, patients receive a second vaccination about a month to 6 weeks after a first vaccination.

In the present disclosure, the term "prevention" refers to any action that inhibits or delays the occurrence, spread and recurrence of the severe fever with thrombocytopenia syndrome by administration of the immunogenic composition according to the present disclosure.

The term "treatment" as used in the present disclosure refers to any action that reduces or beneficially alters the symptoms of the severe fever with thrombocytopenia syndrome and complications thereof via the administration of the immunogenic composition according to the present disclosure. A person with ordinary knowledge in the technical field to which the present disclosure belongs refers to the data presented by the Korean Medical Association, etc. to know the exact criteria about the disease to which the composition according to the present disclosure is effective, and to determine degrees of the improvement and treatment.

The term "therapeutically effective amount" used in combination with an active ingredient in the present disclosure refers to an amount effective for preventing or treating the severe fever with thrombocytopenia syndrome. The therapeutically effective amount of the composition according to the present disclosure may vary depending on several factors, such as administration method, target site, and patient's condition. Therefore, when the composition is used for the human body, the dosage should be determined as an appropriate amount in consideration of safety and efficiency. The skilled person may estimate the amount to be used for humans from an effective amount determined through animal experiments. Factors to consider when determining the effective amount are described, for example, in Hardman and Limbird, eds., Goodman and Gilman's The Pharmacological Basis of Therapeutics, 10th ed. (2001), Pergamon Press; And E. W. Martin ed., Remington's Pharmaceutical Sciences, 18th ed. (1990), Mack Publishing Co.

A pharmaceutical composition according to the present disclosure is administered in a pharmaceutically effective amount. As used in the present disclosure, the term "pharmaceutically effective amount" refers to an amount sufficient to treat the severe fever with thrombocytopenia syndrome at a reasonable benefit/risk ratio applicable to medical treatment and not to cause side effects. The effective dose level may be determined based on factors including the patient's health status, type of transplantation, severity, activity of the drug, sensitivity to the drug, method of administration, time of administration, route of administration and rate of excretion, duration of treatment, drugs used in combination or simultaneously, and other factors well known in the medical field. The composition according to the present disclosure may be administered as an individual therapeutic agent or administered in combination with other therapeutic agents or may be administered sequentially or simultaneously with a conventional treatment agent, or may be administered single or multiple times. Considering all of the above factors, it is important to administer the amount by which the maximum effect may be obtained at the minimum amount without side effects. This amount may be easily determined by a person skilled in the art.

The pharmaceutical composition according to the present disclosure may contain carriers, diluents, excipients or a combination of two or more thereof commonly used in biological preparations. As used in the present disclosure, the term "pharmaceutically acceptable" refers to characteristics that a composition is not toxic to cells or humans as exposed to the composition. The carrier is not particularly limited as long as the carrier is suitable for delivery of the composition to a target site in vivo. The carrier may include, for example, compounds described in Merck Index, 13th ed., Merck & Co. Inc., saline, sterile water, Ringer's solution, buffered saline, dextrose solution, maltodextrin solution, glycerol, ethanol, and mixtures of one or more of these components. If necessary, other conventional additives such as antioxidants, buffers, and bacteriostatic agents may be added thereto. Further, when additionally adding a diluent, a dispersant, a surfactant, a binder, and a lubricant to the composition, the composition may be formulated into a formulation for injection such as an aqueous solution, a suspension, an emulsion, a pill, a capsule, a granule or a tablet. Furthermore, the composition may be preferably formulated based on each disease or component using a method appropriate in the art or by a method disclosed in Remington's Pharmaceutical Science (Mack Publishing Company, Easton PA, 18th, 1990).

In one implementation, the pharmaceutical composition may be formulated into at least one selected from the group including oral dosage forms, external preparations, suppositories, sterile injectable solutions and sprays. Oral or injection formulations are more preferred.

The term "administration" as used in the present disclosure means providing a predetermined substance to a subject or patient in any appropriate way. Depending on the intended method, parenteral administration (for example, an injection formulation being applied in intravenous, subcutaneous, intraperitoneal manner or topically) or oral administration may be possible. The dosage range varies depending on the patient's weight, age, sex, health status, diet, administration time, administration method, excretion rate, and severity of disease. Liquid formulations for oral administration of the composition according to the present disclosure include suspensions, liquid solutions, emulsions, syrups, etc. In addition to water and liquid paraffin, which are commonly used simple diluents, various excipients such as wetting agents, sweeteners, fragrances, and preservative may be contained therein together. Formulations for parenteral administration include sterile aqueous solutions may include non-aqueous solvents, suspensions, emulsions, lyophilized formulations, suppositories, and the like. The pharmaceutical composition according to the present disclosure may be administered using any device capable of delivering the active substance to the target cell. Preferred modes of administration and formulations may be intravenous injections, subcutaneous injections, intradermal injections, intramuscular injections, drop injections and the like. Injectables may be prepared using aqueous solvents such as physiological saline and Ringer solutions, or non-aqueous solvents such as vegetable oils, higher fatty acid esters (e.g., oleic acid ethyl, etc.), alcohols (e.g., ethanol, benzyl alcohol, propylene glycol, glycerin, etc.). It may contain a pharmaceutical carrier such as stabilizers to prevent deterioration (e.g. ascorbic acid, sodium hydrogen sulfite, sodium pyro sulfite, BHA, tocopherol, EDTA, etc.), an emulsifier, a buffer for pH control, and a preservative for preventing the growth of microorganisms (e.g., phenyl mercury nitrate, thimerosal, benzalkonium chloride, phenol, cresol, benzyl alcohol, etc.).

As used in the present disclosure, the term "subject" refers to monkeys, cows, horses, sheep, pigs, chickens, turkeys, quails, cats, dogs, mice, rats, rabbits or guinea pigs, or humans who have the severe fever with thrombocytopenia syndrome. The "specimen" may be whole blood, plasma, serum, urine or saliva isolated therefrom.

The pharmaceutical composition according to the present disclosure may further contain pharmaceutically acceptable additives. The pharmaceutically acceptable additives include starch, gelatinized starch, microcrystalline cellulose, lactose, povidone, colloidal silicon dioxide, calcium hydrogen phosphate, lactose, mannitol, malt, arabic rubber, pregelatinized starch, corn starch, powdered cellulose, hydroxypropyl cellulose, opadry, sodium starch glycolate, lead carnauba, synthetic aluminum silicate, stearic acid, magnesium stearate, aluminum stearate, calcium stearate, sucrose, dextrose, sorbitol, talc, and the like. The pharmaceutically acceptable additive according to the present disclosure is preferably contained in 0.1 parts by weight to 90 parts by weight based on the composition, but is not limited thereto.

In one aspect, the present disclosure relates to an antibody produced in response to immunization using the virus or antigen thereof according to the present disclosure.

The antibody is not only in the form of a whole antibody, but also includes a functional fragment of an antibody molecule. The whole antibody has a structure having two full-length light chains and two full-length heavy chains, and each light chain is connected to a heavy chain via a disulfide bond. A functional fragment of an antibody molecule refers to a fragment that has an antigen-binding function. Examples of antibody fragments may include (i) a Fab fragment composed of a variable region (VL) of a light chain and a variable region (VH) of a heavy chain, a constant region (CL) of a light chain, and a first constant region (CH1) of a heavy chain; (ii) an Fd fragment composed of VH and CH1 domains; (iii) an Fv fragment composed of VL and VH domains of a single antibody; (iv) a dAb fragment composed of a VH domain (Ward E S et al., Nature 341:544-546 (1989)); (v) an isolated CDR region; (vi) an F(ab')2 fragment as a bivalent fragment containing two linked Fab fragments; (vii) a single chain Fv molecule (scFv) bound via a peptide linker that binds the VH domain and the VL domain to each other to form an antigen binding site; (viii) a bispecific single-chain Fv dimer (PCT/US92/09965); and (ix) a diabody as a polyvalent or multispecific fragment produced by gene fusion (WO94/13804), and the like.

In one aspect, the present disclosure relates to a diagnostic kit for the severe fever with thrombocytopenia syndrome virus, the kit containing the severe fever with thrombocytopenia syndrome virus or an antigen thereof, or an antibody against the same.

In one implementation, the kit may contain a virus sample containing the virus according to the present disclosure and a reagent for detecting an antigen-antibody complex. The reagent for detecting the antigen-antibody complex includes reagents for radioimmunoassay, ELISA (Enzyme linked immunosorbent assay) or immunofluorescence analysis.

In one embodiment, the detection of the antigen-antibody complex may be achieved using an Ouchterlony plate simply detecting the antibody and/or antigen via the antigen-antibody binding, western blot, and immuno electrophoresis such as Crossed IE, Rocket IE, Fused Rocket IE, and Affinity IE. Reagents or substances as used in this method are known. This may be detected, for example, via antigen-antibody reactions, or substrates, nucleic acids or peptide aptamers that specifically bind to antigens, or reactions with receptors, ligands, or cofactors interacting with the complex or using mass spectrometry. The reagent or substance that specifically interacts or binds to the antigen-antibody complex of the present application may be used in a chip method or in combination with nanoparticles. The immunoassay or immunostaining method is described in Enzyme Immunoassay, E. T. Maggio, ed., CRC Press, Boca Raton, Florida, 1980; Gaastra, W., Enzyme-linked immunosorbent assay (ELISA), in Methods in Molecular Biology, Vol. 1, Walker, J. M. ed., Humana Press, NJ, 1984. Analyzing the intensity of the final signal by the above-described immunoassay process, that is, performing signal contrast with a normal sample may diagnose absence or presence of the infection of the disease.

In one aspect, the present disclosure relates to a diagnostic composition containing the severe fever with thrombocytopenia syndrome virus or antigen thereof, or an antibody against the antigen.

The compounds according to the present disclosure as used in the diagnostic composition are preferably labeled detectably. Various methods available for labeling biomolecules are well known to those skilled in the art and are considered within the category according to the present disclosure. The methods are described in Tijssen, 'Practice and theory of enzyme immuno assays', Burden, R H and von Knippenburg (Eds), Volume 15 (1985), 'Basic methods in molecular biology'; Davis L G, Dibmer M D; Battey Elsevier (1990), Mayer et al., (Eds) 'Immunochemical methods in cell and molecular biology' Academic Press, London (1987), or in the series 'Methods in Enzymology', Academic Press, Inc.

There are many other marking methods and makers known to the skilled person. Examples of the types of markers that may be used in the present disclosure may be enzymes, radioactive isotopes, colloidal metals, fluorescent compounds, chemiluminescent compounds, and bioluminescent compounds.

Commonly used markers include fluorescent substances (e.g., fluresin, rhodamine, Texas red, etc.), enzymes (e.g. horseradish peroxidase, β-galactosidase, alkaline phosphatase), radioactive isotopes (e.g., $^{32}P$ or $^{125}I$), biotin, digoxigenin, colloidal metal, chemiluminescent or bioluminescent compounds (e.g., dioxetane, luminol or acridinium). The marking methods such as methods based on covalent bonding of enzymes or biotinyl groups, iodination, phosphorylation, and biotinylation are well known in the art.

The detection methods may include autoradiography, fluorescence microscopy, direct and indirect enzyme reactions, etc. but is not limited thereto. A commonly used detection assay may be a radioactive isotope or non-radioactive isotope method. These may include Western blotting, overlay-analysis, Radioimmuno Assay (RIA) and Immuno Radioimmunometric Assay (IRMA), Enzyme Immuno Assay (EIA), Enzyme Linked Immuno Sorbent Assay (ELISA), Fluorescent Immuno Assay (FIA), and Chemioluminescent Immune Assay (CLIA).

In one aspect, the present disclosure relates to a method for detecting a severe fever with thrombocytopenia syndrome virus antibody, the method including contacting a sample isolated from a specimen with a virus or antigen thereof according to the present disclosure under a condition in which an antigen/antibody complex is able to be formed; and detecting formation of an antigen/antibody complex.

In one aspect, the present disclosure relates to a method for producing antiserum against the severe fever with thrombocytopenia syndrome virus in a non-human animal, the method including administering the virus or antigen thereof according to the present disclosure to the non-human animal at an amount effective to induce an immune response; and collecting antiserum or plasma containing an antibody against the severe fever with thrombocytopenia syndrome virus.

In one aspect, the present disclosure relates to a method for providing information regarding the diagnosis of the severe fever with thrombocytopenia syndrome, the method including contacting a sample isolated from a specimen with the virus or antigen thereof according to the present disclosure to form an antigen-antibody complex; and detecting the formation of the complex.

EXAMPLES

The present disclosure is described in more detail based on following Examples. However, the following Examples are intended only for specifying the present disclosure, and the present disclosure is not limited thereto.

Example 1

Virus Isolation

Blood from patients who visited university hospitals and were suspected of having symptoms of severe fever thrombocytopenia syndrome, and bloods from animals (goat and abandoned dogs) suspected of having symptoms of severe fever thrombocytopenia syndrome, and wild mite homogenate were used to identify whether the SFTSV (severe fever thrombocytopenia syndrome virus) thereof is positive/negative via real-time PCR, PCR and ELISA analysis. Specifically, a day before virus infection, VeroE6 cells were dispensed into a 12-well plate, cultured so that the cell density exceeded 60%, and the cells were washed with PBS. The cells were treated with 300 μl of serum from a suspected infected patient (serum obtained by centrifuging whole blood at 3000 rpm for 20 minutes) for 1 hour to infect the cells. After the infection, the serum was removed, and the cells were washed with PBS, and then the cells were exchanged with 1% FBS DMEM medium and cultured in 1% FBS DMEM medium for 2 weeks. The two weeks later, RT-PCR (identification via real-time PCR after reverse transcription) and immune fluorescence assay (in which a mouse SFTSV NP antibody produced in a laboratory was used as the primary antibody and the antibody conjugated with FITC was used as the secondary antibody) were used to identify the presence or absence of the virus isolation. When the virus was not isolated, the virus was isolated by infecting another VeroE6 cell with the first infected supernatant. The isolated viruses were named as CB3/2016, CB7/2017 and CB6/2016.

Example 2

Genetic Analysis of Isolated Virus

The viruses CB3/2016, CB7/2017 and CB6/2016 isolated using Vero E6 cells were respectively reverse-transcribed, and then subjected to PCR, and NGS (next generation sequencing) to identify L, M, S (NP, NS) whole gene sequences thereof. Specifically, RNA was extracted from each virus, and cDNA was produced through reverse-transcription PCR. Subsequently, the L, M, and S genes of each SFTS virus were subjected to PCR to obtain each whole gene. The NGS method was used for gene sequence analysis. The L, M, and S genes of each virus were subjected to tagmentation and index PCR using an illumina nextera XT kit according to the protocol provided from illumina. Afterwards, Fasta Q file of the final sample was generated using the illimina miniseq equipment. The whole gene sequence of the generated file was analyzed using the CLC main workbench program. We integrated the identified gene sequences with the genes of conventional viruses isolated in Korea, China and Japan, and then performed genetic analysis. Thus, it was identified that the SFTSVs CB1, CB3 and CB4 as isolated according to the present disclosure are new genotypes of SFTSV genetically different from the genes of the viruses currently isolated in China or Korea (Yu X J et al., N. Engl. J. Med. 2011) and the virus first isolated in Korea (Gangwon/2012). In addition, it was identified based on a result of a phylogenetic gene analysis of L, M, and S (NP, NS) genes of viruses according to the present disclosure and viruses isolated from Korea, China, and Japan using the MEGA 7.0 program, that the viruses according to the present disclosure were close to the group B which most of the domestic isolated viruses belong to, but the genes L, M and S (NP and NS) thereof are different from those of the conventional viruses. Thus, we identified that the viruses according to the present disclosure is subdivided into at least 3 or more groups (FIG. 1 to FIG. 4). Accordingly, the three genotype SFTSVs isolated according to the present disclosure as subdivided were named B-1 (CB3/2016), B-2 (CB7/2017) and B-3 (CB6/2016), respectively.

Example 3

Figure 5:
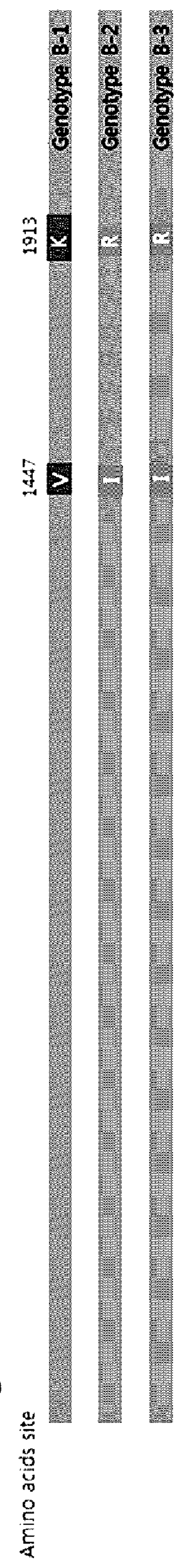
FIG. 5 shows amino acid mutation sites in L and M genes of three novel viruses of genotypes B-1 (CB3/2016), B-2 (CB7/2017) and B-3 (CB6/2016) according to the present disclosure.
Figure 5:
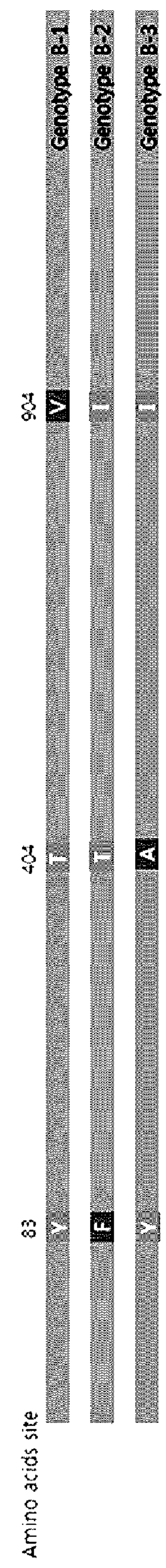

Identification of Differences in Amino Acid Sequence of L, M and S Genes by Viruses 3-1. L Gene Amino Acid Sequence Difference It was identified based on a result of analyzing an amino acid sequence based on the open reading frame (ORF) of each of the L, M and S genes of the viruses of the novel subdivided genotypes B-1, B-2 and B-3 isolated according to the present disclosure, that the L and M genes were different from those in the conventional virus. Specifically, ORF (6255 bp) of an L gene in the B genotype encodes RdRp. In the genotype B-1 virus according to the present disclosure, the 1447-th amino acid of RdRp was valine or the 1913-rd amino acid thereof was lysine. In the genotype B-2 virus and B-3 virus according to the present disclosure, the 1447-th amino acid of RdRp was isoleucine or the 1913-rd amino acid thereof was arginine (FIG. 5A and Table 1).

TABLE 1

| Amino | L gene | | M gene | | |
|---|---|---|---|---|---|
| Acids site | 1447 | 1913 | 83 | 404 | 904 |
| B-1 type | Val | Lys | Tyr | Thr | Val |
| B-2 type | Ile | Arg | Phe | Thr | Ile |
| B-3 type | Ile | Arg | Tyr | Ala | Ile |

3-2. M Gene Amino Acid Sequence Difference

It was identified based on a result of analyzing an amino acid sequences of the L, M and S genes of the viruses of the new subdivided genotypes B-1, B-2 and B-3 isolated in accordance with the present disclosure, the L and M genes were different from those in the conventional virus. Specifically, ORF (3222 bp) of an M gene in the B genotype encodes Gn and Gc proteins. According to the present disclosure, in the genotype B-1 virus, the 83-rd amino acid of ORF of an M gene was tyrosine or the 404-th amino acid thereof was threonine or the 904-th amino acid thereof was valine. In the genotype B-2 virus, the 83-rd amino acid of ORF of an M gene was phenylalanine, the 404-th amino acid thereof was threonine or the 904-th amino acid thereof was isoleucine. In the genotype B-3 virus, the 83-rd amino acid of ORF of an M gene was tyrosine, the 404-th amino acid thereof was alanine, or the 904-th amino acid thereof was isoleucine (FIG. 5B and Table 1).

Example 4

Comparison of Gene Homology Based on Genotype

SFTSVs currently isolated in Korea and SFTSVs of the subdivided genotypes B-1, B-2 and B-3 according to the present disclosure were subjected to genetic analysis. The homology of L, M and S genes based on each genotype was compared and analyzed. As a result, about 96% to 100% of the gene homology (nucleotide level) between the viruses belonging to the same genotype was observed, while 91% to 97% of a relatively low gene homology between different genotype viruses was observed (Tables 2 to 5). Further, in the genotype B-3 group according to the present disclosure, the homology within the same group exhibited a relatively low homology at a level of about 95% to 100%. Thus, the possibility of subdividing the B-3 group into different genotype groups was identified.

TABLE 2

| | Sequence homology (%) (Nucleotide identity) | | |
|---|---|---|---|
| Genotype | B-1 | B-2 | B-3 |
| B-1 | 96.4~100.0% | 96.0~97.4% | 95.9~97.1% |
| B-2 | 98.6~99.6% | 97.2~100.0% | 96.2~97.1% |
| B-3 | 98.1~99.8% | 98.2~99.9% | 96.5~100.0% |

Comparison of Homology of L Gene

TABLE 3

| | Sequence homology (%) (Nucleotide identity) | | |
|---|---|---|---|
| Genotype | B-1 | B-2 | B-3 |
| B-1 | 95.8~100.0% | 94.5~97.1% | 93.2~96.8% |
| B-2 | 98.3~99.6% | 95.7~100.0% | 93.7~96.8% |
| B-3 | 94.8~99.3% | 95.3~99.7% | 94.4~100.0% |

Comparison of Homology of M Gene

TABLE 4

| | Sequence homology (%) (Nucleotide identity) | | |
|---|---|---|---|
| Genotype | B-1 | B-2 | B-3 |
| B-1 | 95.8~100.0% | 94.5~97.1% | 93.2~96.8% |
| B-2 | 98.3~99.6% | 95.7~100.0% | 93.7~96.8% |
| B-3 | 94.8~99.3% | 95.3~99.7% | 94.4~100.0% |

Comparison of Homology of S (NP) Gene

TABLE 5

| | Sequence homology (%) (Nucleotide identity) | | |
|---|---|---|---|
| Genotype | B-1 | B-2 | B-3 |
| B-1 | 95.8~100.0% | 94.8~97.4% | 94.3~96.8% |
| B-2 | 98.9~100.0% | 95.1~100.0% | 94.8~98.2% |
| B-3 | 96.2~100.0% | 94.9~100.0% | 96.1~100.0% |

Comparison of Homology of S (NS) Gene

Example 5

Cross Immunogenic Analysis and Vaccine Effect Identification Based on Genotype 5-1. Cross Immunogenic Analysis Based on Genotype In order to compare and analyze cross immunogenicity based on each genotype, a fifty percent of focus reduction neutralization test (FRNT50) was performed. Specifically, we carried out mass proliferation of viruses of the new subdivided genotype B-1, B-2 and B-3 as isolated according to the present disclosure, and then carried out inactivation thereof by adding formalin (0.05%) thereto, and then identified occurrence or non-occurrence of the inactivation thereof via 3 times virus isolations. The inactivated whole vaccines were used to produce proteins via ultracentrifugation using 20% sucrose. The proteins were immunized into ferrets. After 2 weeks, additional immunization was performed on the ferrets (two times immunizations, 2 weeks intervals), and the blood was collected therefrom and the serum was separated therefrom. The separated serum was inactivated at 56° C. for 30 minutes, diluted to 1/10, and then serially diluted 2 times. The virus diluted with 200 FFU/ml was reacted with the virus as serially diluted at 37° C. at 1:1. After washing the VeroE6 cells as dispensed in a 6-well plate, the cells were infected with the reacted virus. One hour thereafter, we performed washing of the cells. Then, the cells were immersed in 0.8% DMEM agarose gel containing 1% FBS. 5 days after the infection, formalin was used to fix the cells, and 3 hours thereafter, three washes were performed, followed by treatment with 10% triton x-100 for 5 minutes at room temperature. Then, the cells were washed 3 times and blocking thereof was performed with 5% BSA. After incubation of the cells using a produced polyclonal NP antibody as a primary antibody, the cells were washed three times, and the cells were reacted with the HRP conjugated antibody as a secondary antibody for 1 hour, and then were washed, and then colored with DAB to identify the coloring result. The result was interpreted such that up to a value reduced by 50% compared to that of the focus forming of the well infected with only the virus was effective.

TABLE 6

| | Serum | | |
|---|---|---|---|
| Virus | B-1 | B-2 | B-3 |
| B-1 | 1280 | 1280 | 320 |
| B-2 | 640 | 2560 | 320 |
| B-3 | 640 | 640 | 640 |

It was found based on the result of identifying cross-immunogenicity of the B-1, B-2, and B-3, the highest titer was found for each virus as shown in the Table 6. Thus, the viruses belonging to the same genotype exhibited high cross-neutralization reactivity, but the viruses belonging to different genotypes exhibited relatively low cross-neutralization reactivity.

5-2. Vaccine Effectiveness Identification

After proliferating the viruses of the new subdivided genotypes B-1, B-2 and B-3 isolated according to the present disclosure in large quantities, formalin (0.05%) was added thereto to inactivate each virus. Then, whether each virus was successfully inactivated was checked via three times virus isolations. Each of the inactivated whole vaccine was immunized into 5 ferrets twice at 2 weeks intervals, and the ferrets were challenged at $1\times10^{7.6}$/ml for each virus.

Figure 6:
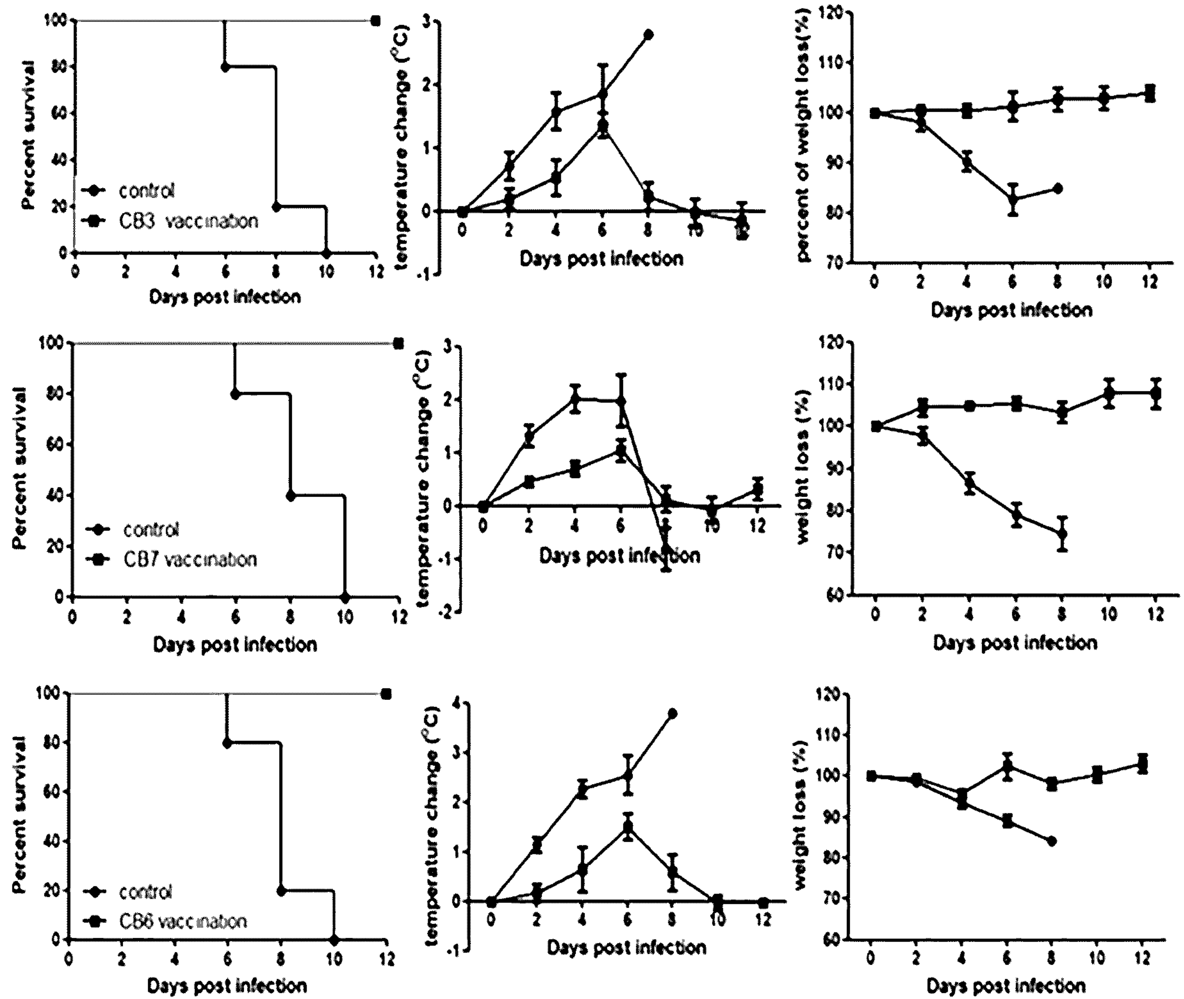
FIG. 6 is a diagram that identifies vaccine effects of three novel viruses of genotypes B-1 (CB3/2016), B-2 (CB7/2017) and B-3 (CB6/2016) according to the present disclosure.

It was identified based on the result of the attack challenge that the control animals died within 10 days of all challenge attack virus infections, but all ferrets of the vaccinated group survived. Body temperature increase and weight loss were identified 2 to 8 days after the infection. Thereafter, they were recovered (FIG. 6).

Summarizing the above results, there are various genotypes of viruses having various genes in SFTSV. The viruses belonging to the same genotype exhibited the relatively high gene homology and high cross-immune response, but the viruses of the different genotypes exhibited the relatively low gene homology and low cross-immunogenicity. Thus, it may be inferred that in order to exhibit the cross-immunogenicity between the various genotypes, only a specific genotype of virus may exhibit limited protective ability.

Therefore, the new viruses CB3/2016, CB7/2017 and CB6/2016 belonging to the subdivided genotypes B-1, B-2 and B-3 according to the present disclosure respectively are useful as vaccines having excellent cross immunogenicity with the SFTSV of the genotype B.

The invention claimed is:

1. An immunogenic composition for prevention or treatment of a severe fever with thrombocytopenia syndrome, comprising inactivated severe fever with thrombocytopenia syndrome virus or a gene thereof as an active ingredient, and an adjuvant, wherein the severe fever with thrombocytopenia syndrome virus or the gene thereof comprises:

(i) a L gene that encodes a protein having the sequence of SEQ ID NO: 13;

(ii) a M gene that encodes a protein having the sequence of SEQ ID NO: 14, (iii) a NP gene that encodes a protein having the sequence of SEQ ID NO: 15 and (iv) a NS gene that encode a protein having the sequence of SEQ ID NO: 16.

2. The composition of claim 1, wherein the severe fever with thrombocytopenia syndrome virus contains an L gene containing a base sequence represented by SEQ ID NO: 1, an M gene containing a base sequence represented by SEQ ID NO: 2, an NP gene containing a base sequence represented by SEQ ID NO: 3, and an NS gene containing a base sequence represented by SEQ ID NO: 4.

3. The composition of claim 1, wherein the composition further comprises a pharmaceutically acceptable carrier.

4. A method for detecting a severe fever with thrombocytopenia syndrome virus antibody, the method comprising:

(a) contacting a sample isolated from a specimen with severe fever with thrombocytopenia syndrome virus or a gene thereof under a condition in which an antigen-antibody complex is able to be formed; and (b) detecting the formation of the antigen-antibody complex, wherein the severe fever with thrombocytopenia syndrome virus, or the gene thereof comprises (i) a L gene that encodes a protein having the sequence of SEQ ID NO: 13;

(ii) a M gene that encodes a protein having the sequence of SEQ ID NO: 14, (iii) a NP gene that encodes a protein having the sequence of SEQ ID NO: 15 and (iv) a NS gene that encode a protein having the sequence of SEQ ID NO: 16.

5. A method for producing antiserum against a severe fever with thrombocytopenia syndrome virus in a non-human animal, the method comprising:

(a) administering severe fever with thrombocytopenia syndrome virus or a gene thereof to the non-human animal at an amount effective to induce an immune response; and (b) collecting antiserum or plasma containing an antibody against the severe fever with thrombocytopenia syndrome virus, wherein the severe fever with thrombocytopenia syndrome virus or the gene thereof comprises (v) a L gene that encodes a protein having the sequence of SEQ ID NO: 13;

(vi) a M gene that encodes a protein having the sequence of SEQ ID NO: 14, (vii) a NP gene that encodes a protein having the sequence of SEQ ID NO: 15 and (viii) a NS gene that encode a protein having the sequence of SEQ ID NO: 16.

* * * * *